US007690953B2

(12) United States Patent
Boyd et al.

(10) Patent No.: US 7,690,953 B2
(45) Date of Patent: Apr. 6, 2010

(54) STACKABLE ELECTRICAL CONNECTION APPARATUS

(75) Inventors: Garth W. Boyd, Ellington, CT (US); Aaron Engel, Wethersfield, CT (US); Dana Dubuc, Tarpon Springs, FL (US); Edward F. Smith, III, Madison, CT (US); Michael E. Poppy, New Richmond, WI (US)

(73) Assignee: Deringer-Ney, Inc., Bloomfield, CT (US)

( * ) Notice: Subject to any disclaimer, the term of this patent is extended or adjusted under 35 U.S.C. 154(b) by 105 days.

(21) Appl. No.: 12/061,246

(22) Filed: Apr. 2, 2008

(65) Prior Publication Data
US 2008/0274651 A1 Nov. 6, 2008

Related U.S. Application Data

(60) Provisional application No. 60/915,765, filed on May 3, 2007.

(51) Int. Cl.
*H01R 9/22* (2006.01)
(52) U.S. Cl. ...................................... 439/717; 439/909
(58) Field of Classification Search ................. 439/717, 439/709, 712, 701, 721, 909, 827; 607/37
See application file for complete search history.

(56) References Cited

U.S. PATENT DOCUMENTS 3,001,170 A * 9/1961 Eyre et al. ................... 439/717
3,848,951 A 11/1974 Michaels et al.
6,878,013 B1 * 4/2005 Behan ........................ 439/668
6,895,276 B2 * 5/2005 Kast et al. ..................... 607/37
6,929,517 B2 * 8/2005 Tsai ............................ 439/810

(Continued)

FOREIGN PATENT DOCUMENTS

EP 1 737 078 A1 12/2006

(Continued)

OTHER PUBLICATIONS

Harris et al., "A study of some palladium-tin, silver-tin and palladium-silver-tin alloys", Journal of the Less-Common Metals, Elsevier-Sequoia, S.A. Lausanne, CH, vol. 16, No. 3, Nov. 1, 1968 (pp. 223-232).

(Continued)

*Primary Examiner*—Hae Moon Hyeon
(74) *Attorney, Agent, or Firm*—Bridget M. Hayden; Dorsey & Whitney LLP

(57) ABSTRACT

An electrical connection apparatus includes at least one stackable block operably coupleable to another stackable block, at least one pin receiving portion defined by an inner wall within the stackable block, and at least one electrical connection contact having a C-shaped contact portion with elastic properties disposed within the pin receiving portion and a lead portion disposed at a location exterior to the stackable block. The electrical connection apparatus may further include an adjustment component and an adjustment component receiving portion defined by in inner wall within the stackable block. In addition, sliders may be arranged on the stackable block and may engage with tabs formed on the at least one electrical connection contact. The sliders may be moved to a raised or lowered position in order to move the at least one electrical connection contact between a contact and an insertion position.

30 Claims, 23 Drawing Sheets

U.S. PATENT DOCUMENTS

| | | | |
|---|---|---|---|
| 7,070,455 B2* | 7/2006 | Balsells | 439/668 |
| 7,087,077 B1 | 8/2006 | Van Dijk et al. | |
| 7,128,757 B2 | 10/2006 | Boylan et al. | |
| 7,195,523 B2* | 3/2007 | Naviaux | 439/827 |
| 7,510,447 B2* | 3/2009 | Drew | 439/669 |
| 7,526,339 B2* | 4/2009 | Lahti et al. | 607/37 |
| 2001/0053631 A1 | 12/2001 | Nagai | |
| 2002/0002016 A1 | 1/2002 | Sato et al. | |
| 2004/0153138 A1 | 8/2004 | Murphy | |
| 2005/0186829 A1* | 8/2005 | Balsells | 439/352 |
| 2007/0162108 A1 | 7/2007 | Carlson | |
| 2007/0225772 A1* | 9/2007 | Lahti et al. | 607/37 |
| 2007/0280850 A1 | 12/2007 | Carlson | |
| 2008/0195194 A1 | 8/2008 | Pacetti et al. | |

FOREIGN PATENT DOCUMENTS

| | | |
|---|---|---|
| WO | WO 02/095877 A1 | 11/2002 |
| WO | WO 2007/070544 | 6/2007 |

OTHER PUBLICATIONS

Schenck, J.F., "The Role of Magnetic Susceptibility in Magnetic Resonance Imaging: MRI Magnetic Compatibility of the First and Second Kinds", Medical Physics, AIP, Melville, NY, US, vol. 23, No. 6, Jun. 1, 1996.

Partial International Search Report (5pgs).

http://www.integra-ls.com/products/?product=55 website, first published Aug. 16, 2004.

* cited by examiner

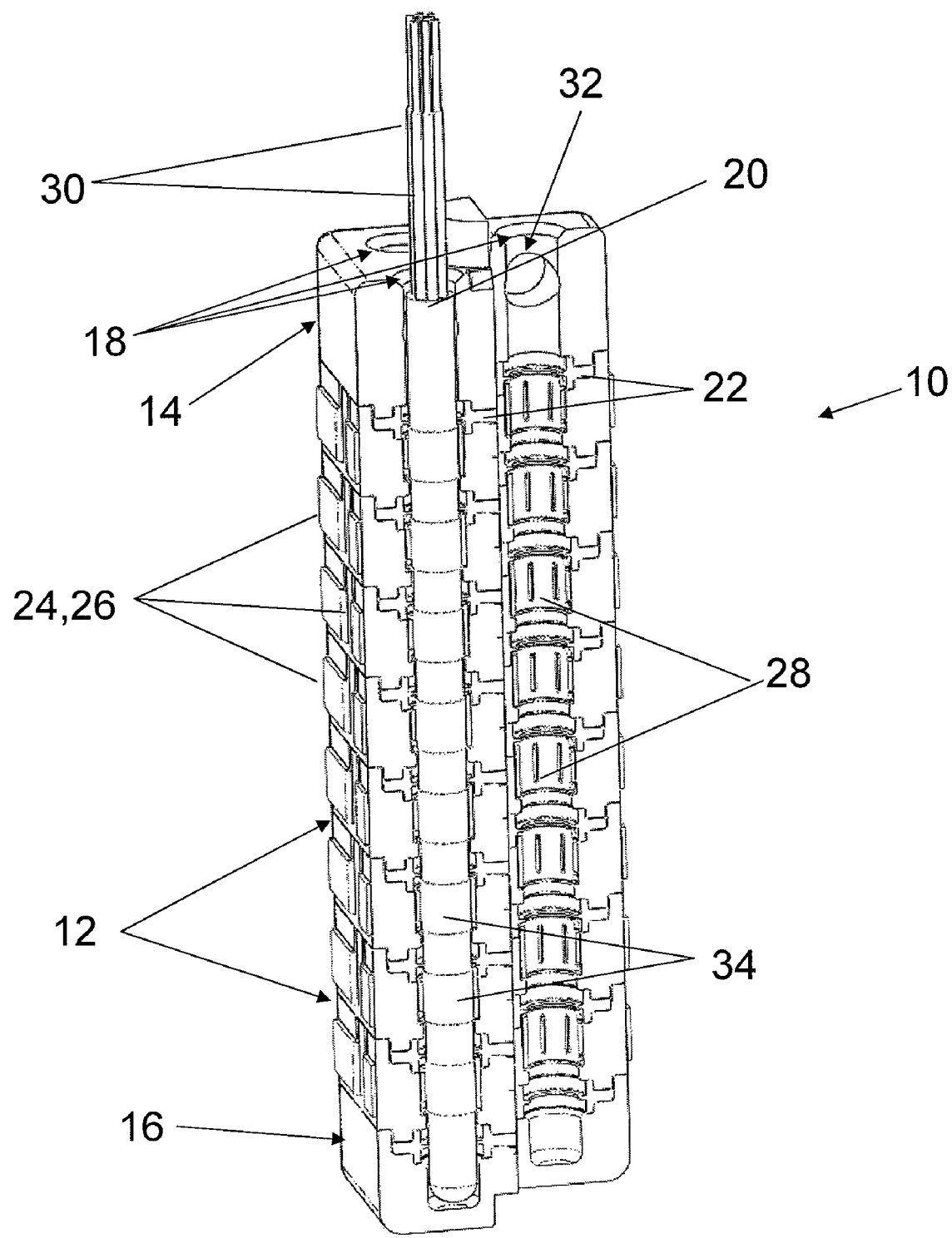

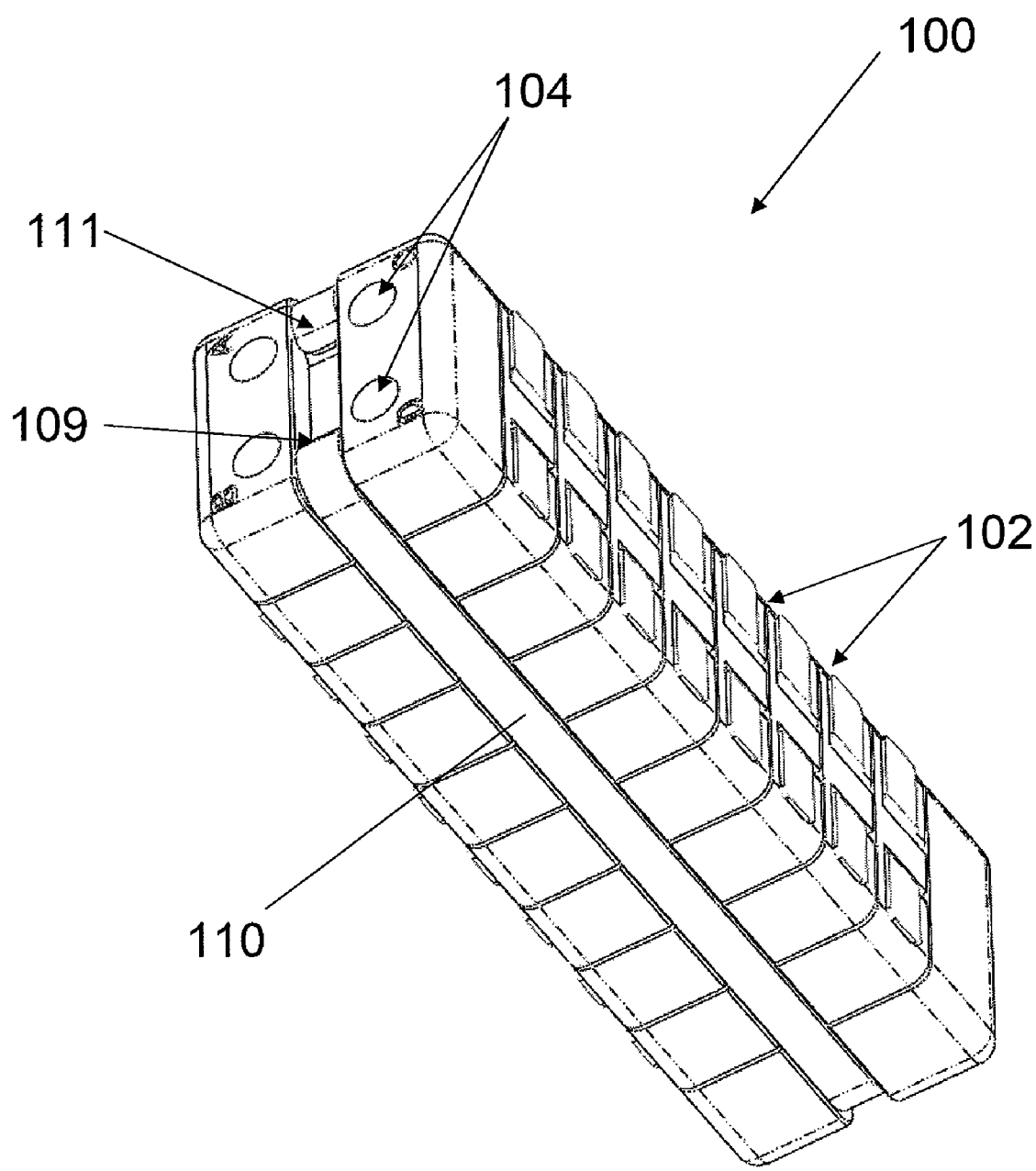

102

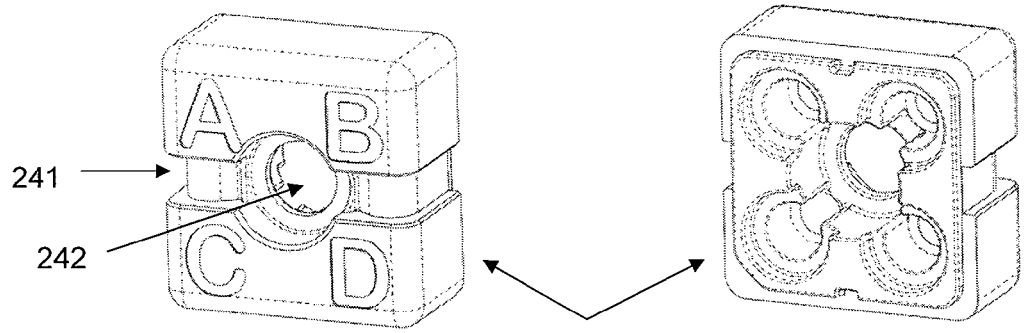
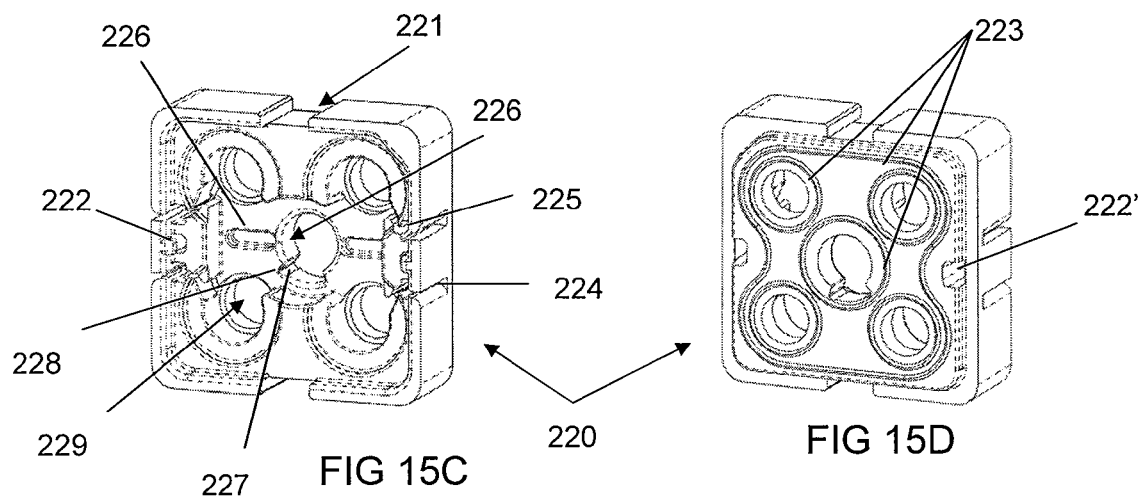
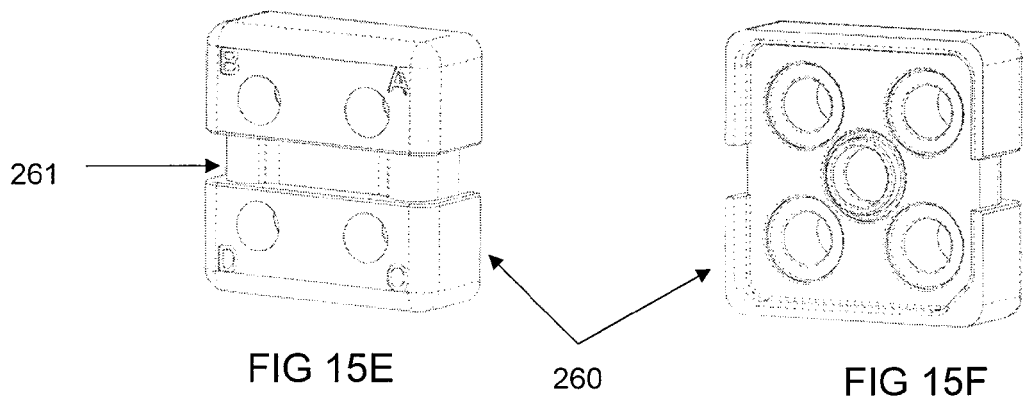

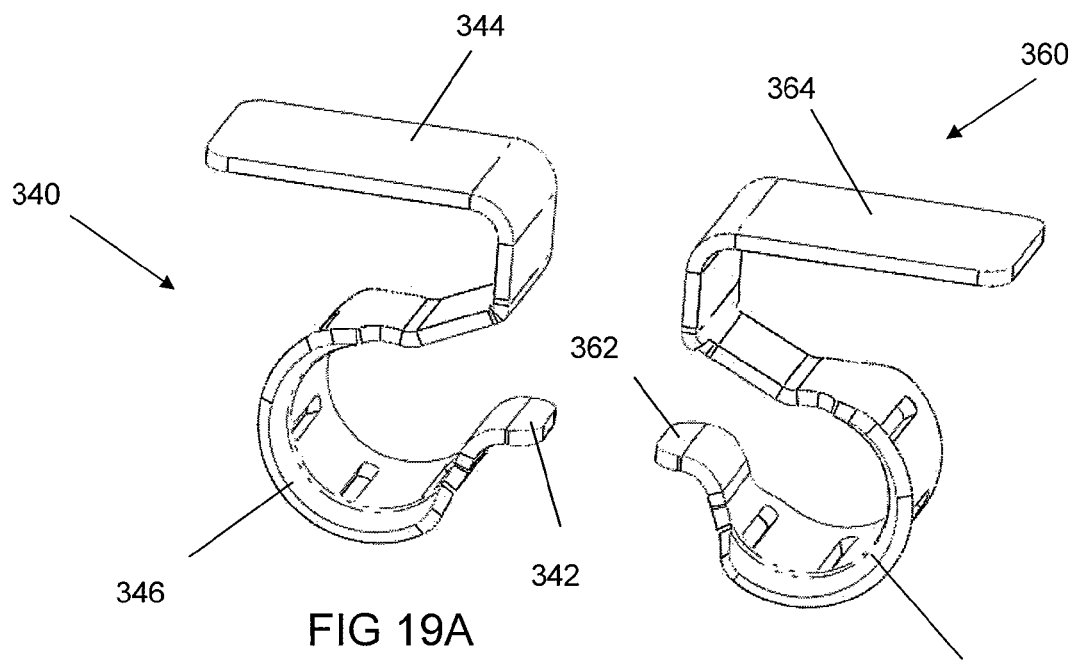
FIG 19A
FIG 19B
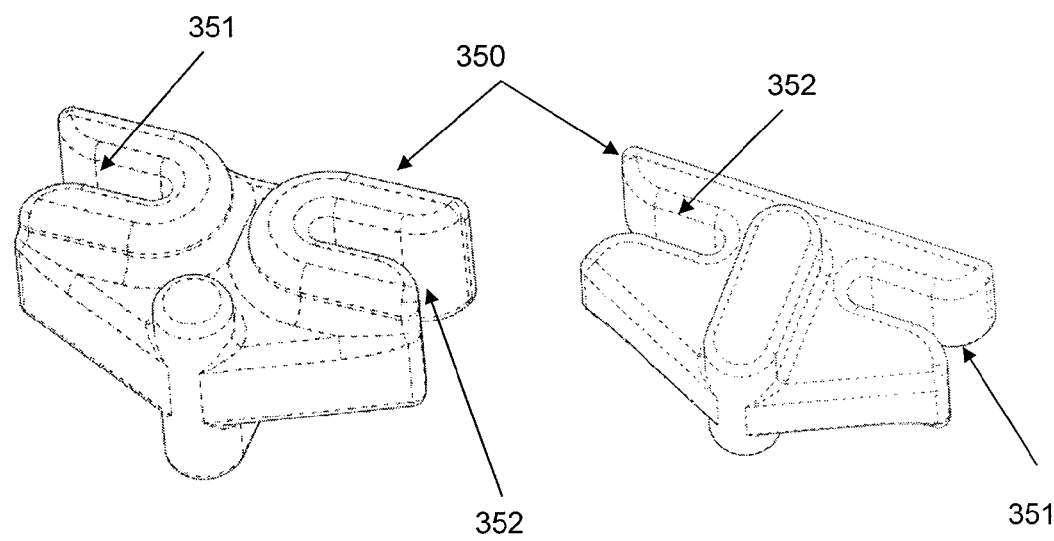
FIG 20A
FIG 20B

STACKABLE ELECTRICAL CONNECTION APPARATUS

CROSS REFERENCE TO RELATED APPLICATION

This application claims benefit under 35 U.S.C. § 119(e) to U.S. Ser. No. 60/915,765, entitled "Electrical Connection Apparatus", filed May 3, 2007 the content of which is incorporated herein by reference in its entirety.

FIELD OF THE INVENTION

The present invention relates to an electrical connection apparatus, and in particular, relates to an electrical connection apparatus for use with implantable medical devices and components associated with implantable medical devices.

BACKGROUND

Active implantable medical devices often are associated with implantable leads that electrically couple to the implantable device to a power supply or signal generator. One problem in implementing medical leads in an implantable medical device is establishing and maintaining a stable, low noise electrical connection between the components. An electrical connection apparatus may facilitate the electrical coupling required for the implantable device to work in concert with the implantable leads. In addition to providing the electrical connection between devices, electrical connection apparatuses may include sealing components that provide isolation between electrical contact structures. However, some apparatuses for providing an electrical connection may not physically lock the connection in place or may not secure the lead position to an extent desired. For example, some leads may be loosely fitted on or in an electrical connection apparatus, and as a result, forces exerted on the lead such as pulling or twisting forces associated with muscle movement, etc. may cause the lead to loosen, create increased signal noise or completely disconnect from the electrical connection apparatus. Accordingly, there is a need to provide an electrical connection apparatus that securely couples to implantable leads.

SUMMARY

An electrical connection apparatus according to one implementation includes at least one stackable block operably coupleable to another stackable block, at least one pin receiving portion defined by an inner wall within the stackable block, and at least one electrical connection component having a C-shaped contact portion with elastic properties disposed within the pin receiving portion and a lead portion disposed at a location exterior to the stackable block, where the C-shaped contact portion and the lead portion integrally form the electrical connection component.

Yet another implementation of an electrical connection apparatus includes at least one stackable block operably coupleable to another stackable block, at least one means for receiving an insertable pin that is defined by the at least one stackable block, and at least one means for providing an electrical connection between an insertable pin and an external device, where the means for providing an electrical connection is disposed in the at least one stackable block.

A method of electrically connecting an implanted medical device and an implanted stimulation electrode according to certain implementations includes providing a connection device having at least one stackable block and a first end block and a second end block arranged on a first and a second end of the at least one stackable block, where each of the stackable blocks includes at least one pin receiving portion defined by the stackable block; and at least one electrical connection contact, where the electrical contact includes a C-shaped contact portion disposed within the at least one pin receiving portion, the C-shaped contact portion having elastic properties; and a lead portion disposed at a location exterior to the stackable block; inserting a pin into the at least one pin receiving portion, wherein the pin is electrically coupled to one of the implanted medical device or the implanted stimulation electrode, and electrically coupling to the lead portion the other of the implanted medical device or the implanted stimulation electrode.

While multiple embodiments of the present invention are disclosed herein, still other embodiments of the present invention will become apparent to those skilled in the art from the following detailed description, which shows and describes illustrative embodiments of the invention. As will be realized, by those of ordinary skill in the art upon reading the following disclosure, the invention is capable of modifications in various aspects, all without departing from the spirit and scope of the present invention. Accordingly, the drawings and detailed description are to be regarded as illustrative in nature and not restrictive.

BRIEF DESCRIPTION OF THE FIGURES

FIG. 1 is cutaway view of one embodiment of an electrical connection apparatus.

FIG. 10 depicts an electrical connection apparatus according to another implementation.

FIGS. 15A-F depict perspective views of a first and second side of a first end block, a stackable block and a second end block of the apparatus of FIGS. 14A-B.

FIGS. 19A-B depict perspective views of electrical connection contacts for use on a left and a right side of the stackable block.

FIGS. 20A-B depict perspective views of a first and second side of a slider for use with the stackable block.

DETAILED DESCRIPTION

Figure 2A:
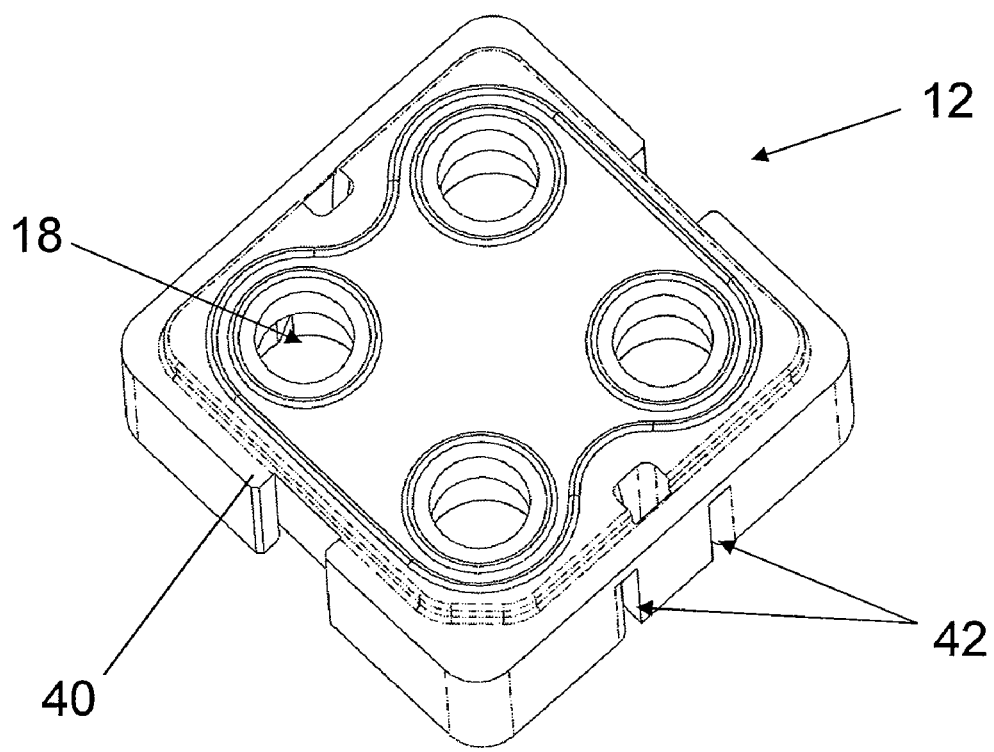
FIGS. 2A-B depict a first side and a second side of a connector block.

The present invention, according to one embodiment, is an electrical connection apparatus.

In one aspect, an electrical connection apparatus may be used in conjunction with implantable medical devices such as neurostimulators or pacemakers. For example, such an apparatus may be used to provide an electrical connection between the implanted device and an implanted stimulation electrode. In one embodiment, the implanted device is a pacemaker. Alternatively, the implanted device may be an implantable cardioverter defibrillator ("ICD"), an implantable pulse generator, or any other implanted device requiring an electrical connection.

FIG. 1 is a cutaway view of one embodiment of an electrical connection apparatus 10. The apparatus is comprised of stackable blocks 12 connected in a stacked fashion, with end blocks 14, 16 disposed at each end. Each block 12, 14, 16 defines pin receiving portions 18 configured to receive a pin such as pin 20 depicted in FIG. 1. In addition, a seal component 22 is disposed between each block 12,14,16. Each block 12, in this implementation, also has electrical connection contacts 24 having exterior contact points 26 (also referred to herein as "leads") disposed on an exterior portion of the device 10 and C-shaped interior contact portions 28 disposed within the pin receiving portions 18.

Generally, the connection apparatus 10 depicted in FIG. 1 connects two devices or components in the following fashion. The pin 20, which is electrically coupled to one device via the lead wires 30, is positioned in one of the pin receiving portions 18 and thereby contacts one or more of the interior contact portions 28 of the electrical connection contacts 24. The other device is positioned or configured such that it is in electrical contact with one more of the exterior contact portions 26 of the electrical connection contacts 24. Thus, the two devices are electrically coupled to each other via the electrical connections contacts 24 disposed within each block 12 of the apparatus 10.

In the embodiment depicted in FIG. 1, the apparatus 10 has eight connector blocks 12. However, it is understood that the apparatus 10 may be comprised of one block 12, two blocks 12, or any number of blocks 12 in order to provide a connection device 10 with the desired size and configuration. End blocks 14, 16 may be used as the end termination for each end of the electrical apparatus 10. End block 14 is also referred to herein as an "insertion end block," while end block 16 is also referred to herein as an "end cap block." The blocks 14, 16 may be manufactured out of metals such as titanium, stainless steel or other biocompatible metals or metallic alloys. Alternatively, the blocks 12, 14, 16 may be made of biocompatible thermoset or thermoplastic resins, or any other known biocompatible material for use in connection devices According to the implementation depicted in FIG. 1, the insertion end block 14 defines mechanical fastening ports 32 for each of the pins 20. Each port 32 may be configured to be in communication with one of the pin receiving portions 18 such that each port 32 may receive a fastening component (not shown) that may be used to fasten or otherwise secure the pin 20 into its position in that pin receiving portion 18. In one embodiment, the fastening component is a threaded set screw made from biocompatible material and each port 32 is a threaded hole configured to receive such a set screw. Alternatively, any known fastening component may be incorporated into the insertion end block 14. In one implementation, a cap or other type of cover may be provided and positioned over the fastening port 32, thereby presenting a relatively smooth external profile for the device 10. In a further alternative, the insertion end block 14 has no fastening ports or fastening components, and the pin 20 is at least partially secured within the pin receiving portions via frictional forces created by contact with the C-shaped contact portions 28.

In use, and in accordance with one aspect, after the pin 20 is positioned in the pin receiving portion 18, the set screw is threaded into the port 32 such that the set screw contacts the pin 20 at an electrically isolated portion of pin 20, and secures pin 20 in the pin receiving portions 18. It acts to supplement the frictional forces exerted by the C-shaped contact portions 28 and helps prevent outward migration of the pin from the housing caused by vibration or excessive tensile or torsional forces on the pin 20 or lead wires 30 during use.

In one implementation as shown in FIG. 1, pin 20 has electrically-isolated circumferential contacts 34 distributed along its length. When the pin 20 is positioned in a pin receiving portion 18, each of the circumferential contacts 34 are positioned to correspond with and contact a C-shaped contact portion 28. Each circumferential contact 34 is electrically connected to one of the lead wires 30, each of which is embedded in the pin 20. Each individual wire or lead 30 may be potted within the pin 20 and may be electrically isolated and insulated from other leads. The pin 20 may contain one or more separate isolated lead wires 30 for each contact 34. Each wire 30 may be capable of maintaining signal integrity from the circumferential contact area 34 through the wire 30 and to a desired location within the body, such as a target tissue, nerve, or some other target area. In one embodiment, a wire 30 terminates with a specialized electrode (not shown) to improve signal delivery to the desired location.

Figure 2B:
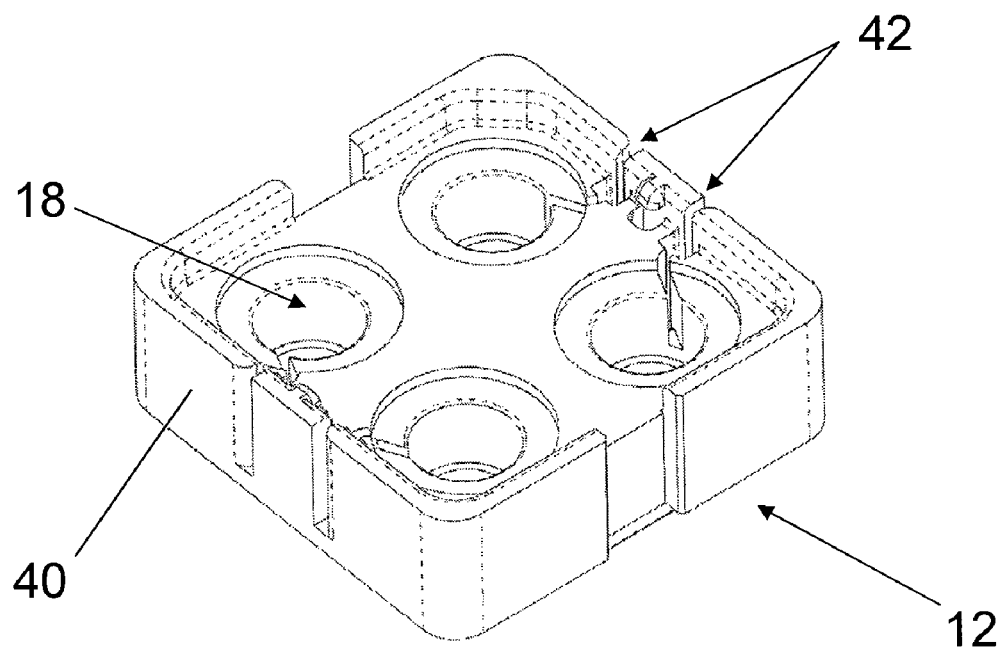
Figure 3A:
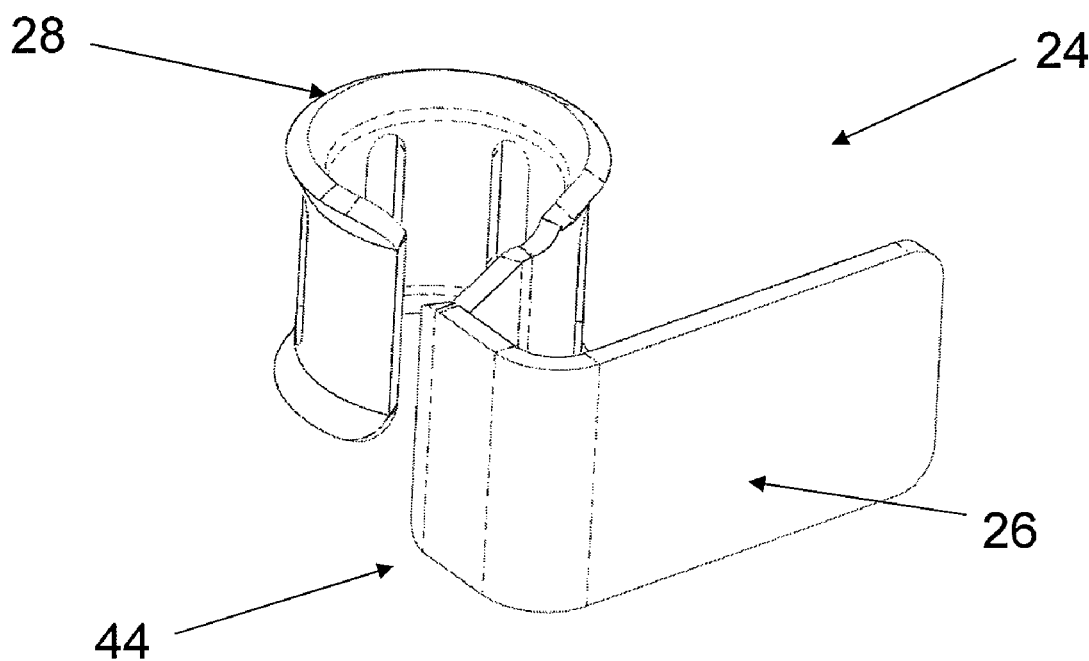
FIGS. 3A-B depict electrical connection contacts according to certain implementations.
Figure 3B:
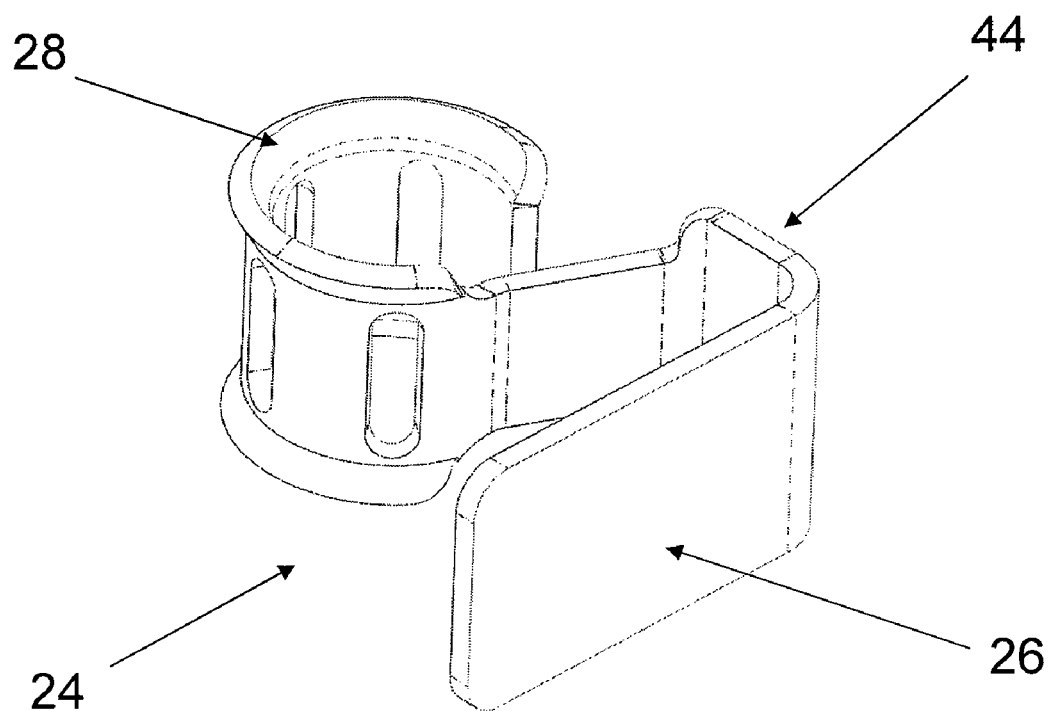

The configuration of a connector block 12 with electrical connection contacts 24, according to one embodiment, is shown in FIGS. 2A, 2B, 3, 4A, and 4B. FIGS. 2A and 2B depict both sides of a connector block 12 without electrical connection contacts, with FIG. 2A depicting a first side and FIG. 2B depicting a second side. The block 12 has a housing 40 that defines the pin receiving portions 18 and further defines slots or passages 42 in which portions of the electrical connection contacts may be disposed.

FIG. 3 depicts an electrical connection contact 24, in accordance with one implementation. The electrical connection contact 24 in this embodiment has a C-shaped contact portion 28 and an external lead portion 26. The contact portion 28 and lead portion 26 are connected via the link portion 44. In one embodiment as shown in FIG. 3, the C-shaped contact portion 28 defines slots or gaps. Alternatively, the contact portion 28 is a continuous, solid component with no slots or gaps.

Figure 4A:
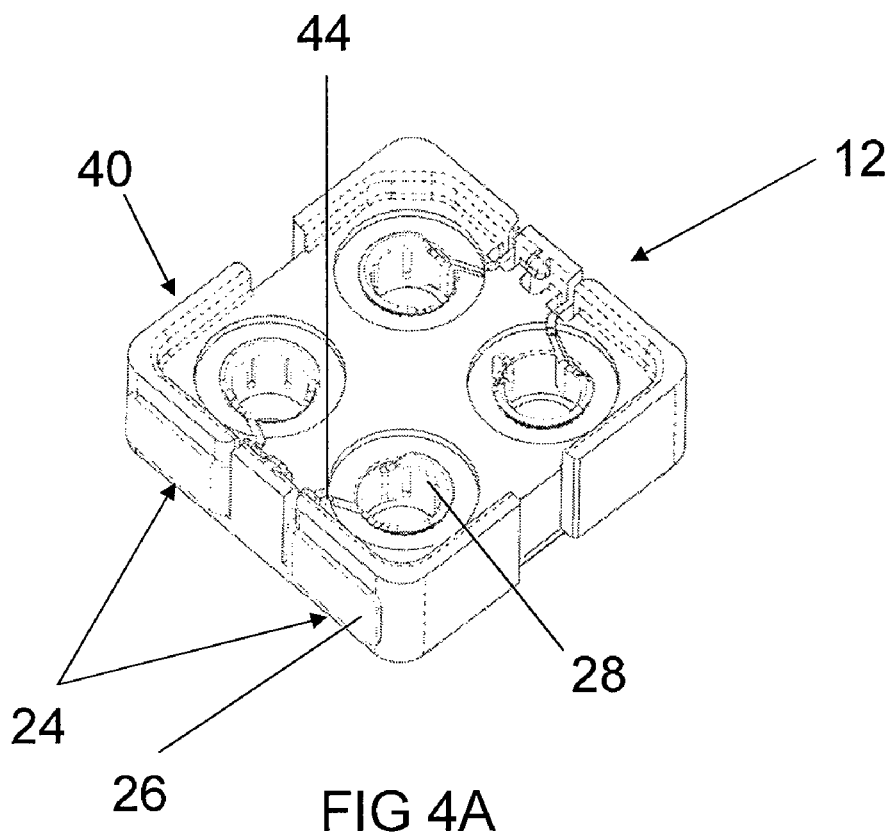
FIGS. 4A-B depict a first and second side of a connector block with four electrical connection contacts according to certain implementations.
Figure 4B:
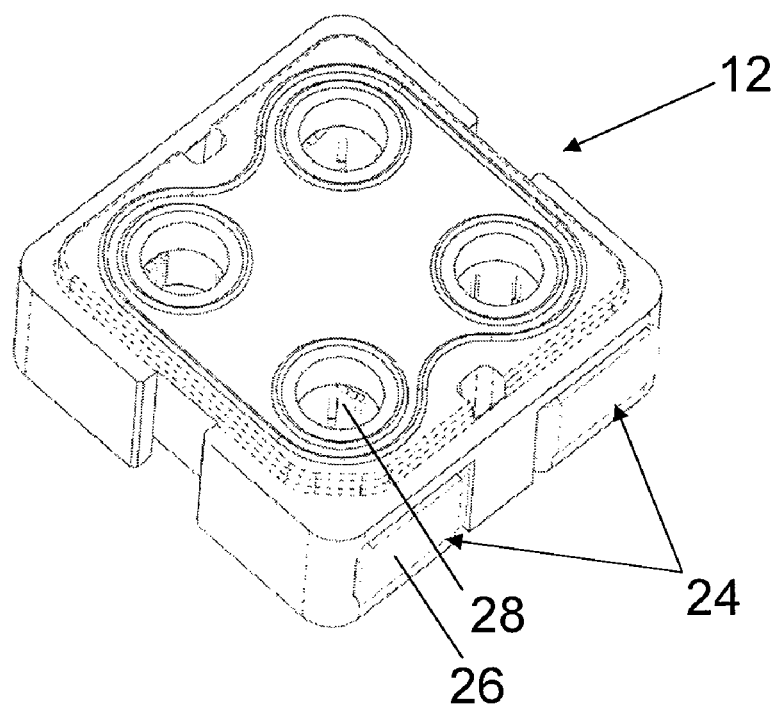
Figure 5E:
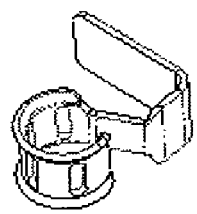
FIGS. 5A-5F depict additional embodiments of electrical connection contacts.
Figure 5D:
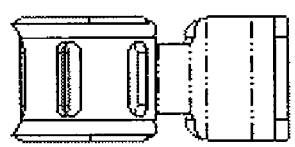
Figure 5F:
Figure 5B:
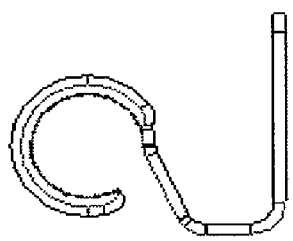
Figure 5C:
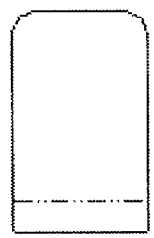
Figure 5A:
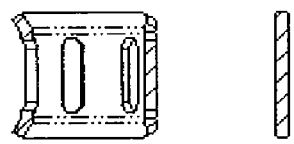

FIGS. 4A and 4B depict a first and second of connector block 12 with four electrical connection contacts 24, according to certain embodiments. Each electrical connection contact 24 may be positioned such that the C-shaped interior contact portion 28 is disposed within a pin receiving portion 18, the exterior contact portion 26 may be disposed on an exterior portion of the housing 40, and the link portion 44 may be disposed in one of the slots 42 as discussed above with respect to FIGS. 2A and 2B.

Each of the contact portions 28, according to one embodiment, is configured to contact any pin positioned in the pin receiving portion 18. In one embodiment, each contact portion 28 contacts a corresponding pin contact area 34 on the pin 20. Such contact results in an electrical connection between the lead 30 and the exterior contact points 26, via the electrical path from the lead 30 to the pin contact area 34 to the contact portion 28 to the link portion 44 to the exterior contact portion 26.

In accordance with one implementation, each C-shaped contact portion 28 is configured to have elastic properties and to have an unconstrained diameter (also referred to as its "unconstrained position," "natural position," "starting position," or "original position") that is smaller than the outside diameter ("OD") of the pin 20. "Elastic properties" as used herein means capable of recovering shape after deformation. Thus, when a pin 20 is positioned in the pin receiving portion 18, the contact portion 28 is deformed from its unconstrained diameter to a larger diameter that accommodates the pin 20. The elasticity of the contact portion 28 urges it back toward its unconstrained diameter such that the contact portion 28 is forced into contact with the pin 20 and results in a normal force being exerted across the contact interface. According to one embodiment, the contact portion 28 is forced into contact with a circumferential contact portion 34 on the pin 20. When the pin 20 is removed, the elastic properties of the contact portion 28 cause the contact portion 28 to return to its unconstrained diameter.

In another embodiment, the C-shaped contact portion 28 also has a maximum diameter that is limited by the diameter of the pin receiving portion 18. That is, the contact portion 28 may only expand to its maximum diameter, at which diameter the contact portion 28 is in contact with the walls of the pin receiving portion 18 and cannot expand further.

FIGS. 5A-5F depict additional embodiments of electrical connection contacts.

According to one embodiment, the electrical connection contacts are made out of a precious metal. For example, the contacts may be constructed of a platinum or PGM (Platinum Group Metal) alloy such as, but not limited to, Pt-10% Ir, Pt-20%Ir, Pt-8%W, Paliney® 500, Paliney® 1100, or Paliney® 1200. Alternatively, the contacts may be formed out of a base metal such as a copper alloy or stainless steel that is overplated with an appropriate electrically and environmentally stable contact material such as Au, Pt, Pd, Pd—Ni, etc. It is also envisioned that the overplate might cover the entire connection 24 or just the terminal contacts 26, 28. According to one embodiment, one advantage of precious metal contact surfaces in comparison to other conductive materials is that the precious metal contact surfaces are capable of maintaining stable electrical signal integrity at reduced force levels. This results in reduced force requirements at the mating of the contact portion 28 and the pin 20, thereby allowing for greater design flexibility in selecting the spring characteristics of the contact member 28. Alternatively, the electrical connection contacts may be made out of a non-PGM metal such as stainless steel, niobium, tantalum, MP35N, or other such non-PGM metals. Certain of these non-PGM metals may require higher contact forces to maintain a stable interface, which may be accomplished by selecting a material with a higher elastic modulus and/or a higher yield stress or by increasing the thickness of the spring member.

The seal component 22, as depicted in FIG. 1 according to one embodiment, is configured to be disposed between any two blocks (including the end blocks) and operates to create two seals. The first seal is a seal between the pin 20 and the rest of the block 12. The second seal is a seal between two connected blocks 12 and associated pin contact areas 34.

Figure 6:
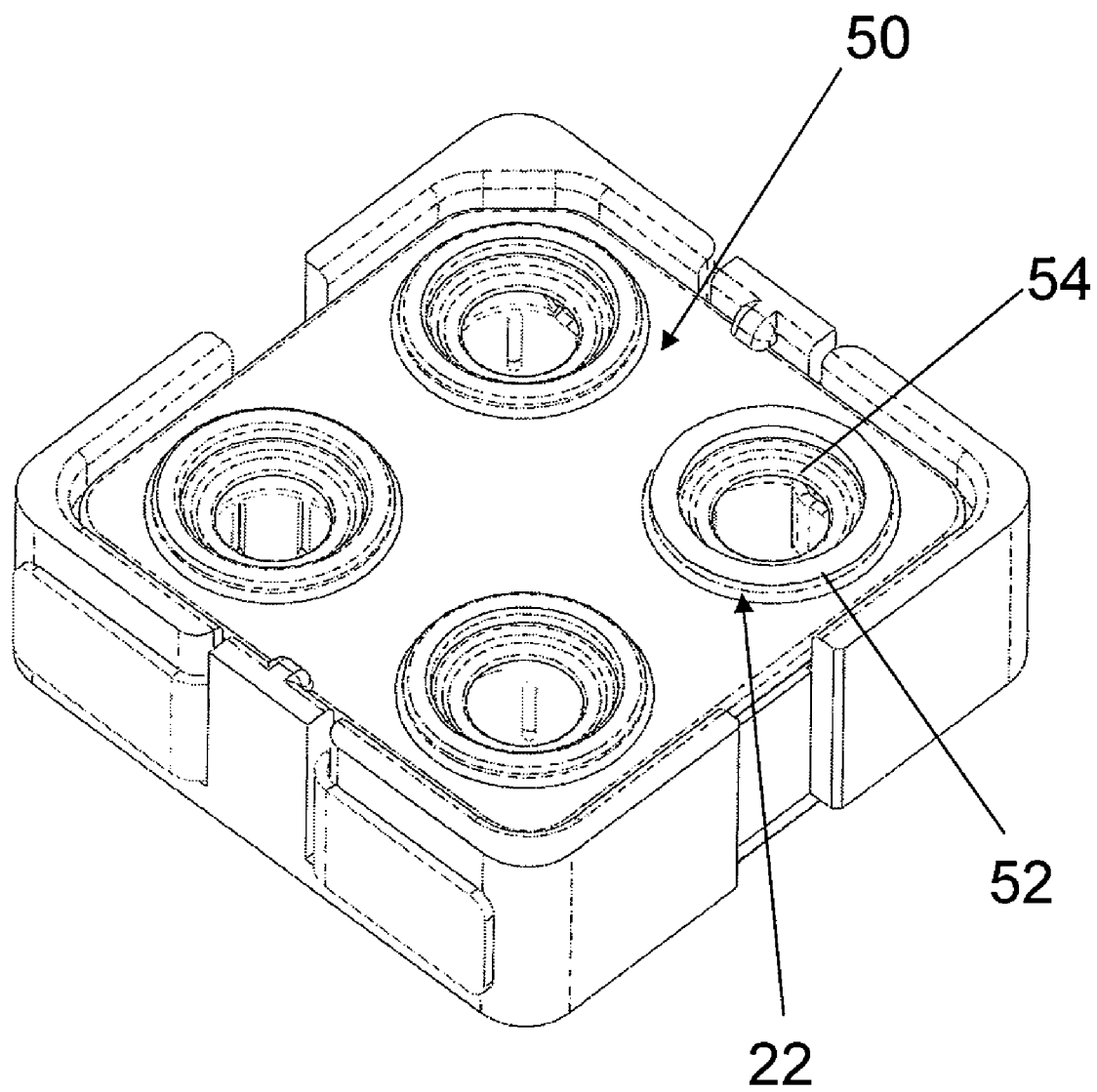
FIG. 6 depicts a seal component according to certain implementations.
Figure 7:
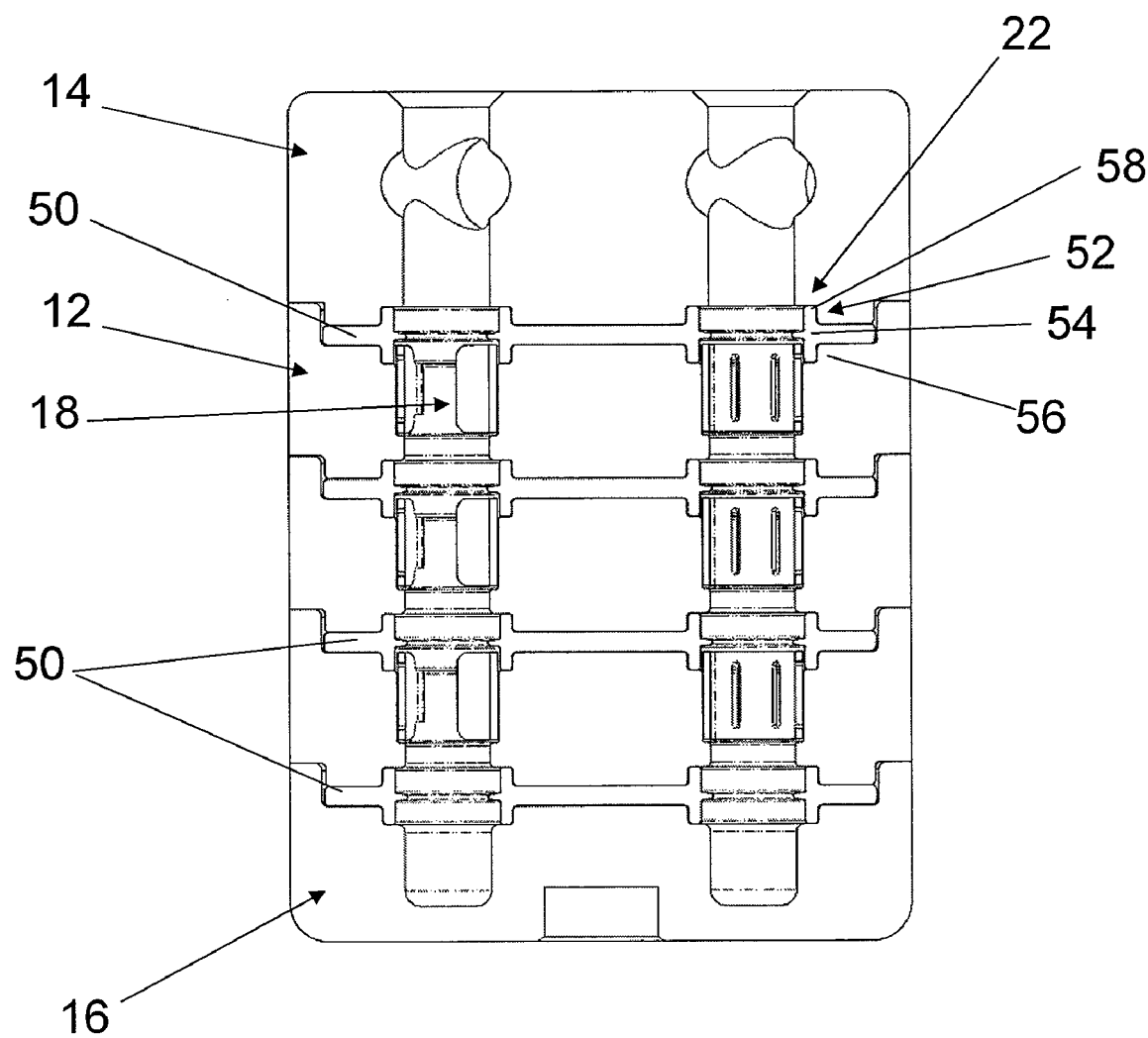
FIG. 7 depicts a seal component according to another implementation.

FIGS. 6 and 7 depict a seal component 22, according to another embodiment. In the embodiment depicted in FIG. 6, a seal plate 50 having four seal components 22 is positioned on one side of a connector block 12. Each seal component 22 disposed in the plate 50 has a "vertical" seal 52 and a "horizontal" seal 54 that completely encircle the pin 20 receiving portion 18 of the block 12. The terms "vertical" and "horizontal" are used solely to describe the seals with respect to each other and the connector blocks and are not intended to be limiting. It is understood that the vertical seal 52 could also be positioned horizontally and that the horizontal seal 54 could also be positioned vertically, depending on the disposition of the entire block. The combination of seals 52 and 54 result in a t-shaped seal component.

As best shown in FIG. 7, the vertical seal 52 of seal component 22 arranged in seal plate 50 provides a seal between the pin receiving portion 18 and the areas exterior to the pin receiving portion 18. In one embodiment, one end 56 of the vertical seal 52 contacts the block 12 next to which the plate 50 has been positioned and the other end 58 of the seal 52 contacts the adjacent block 14. According to one embodiment, the vertical seal 52 may form a seal that prevents body fluids from entering into the pin receiving portion 18, which may cause a short. In accordance with one implementation, the horizontal seal 54 of seal component 22 contacts any pin positioned in the pin receiving portion 18 and thereby provides a seal in the pin receiving portion 18 between blocks 12 and 14. As depicted by the positioning of seal plates 50 in FIG. 7, and in view of the discussion above, it should be understood that seal plate 50 may also be provided between adjacent stackable blocks 12 and between blocks 12 and 16.

Figure 8A:
FIGS. 8A-8D depict additional embodiments of seal components.
Figure 8B:
Figure 8C:
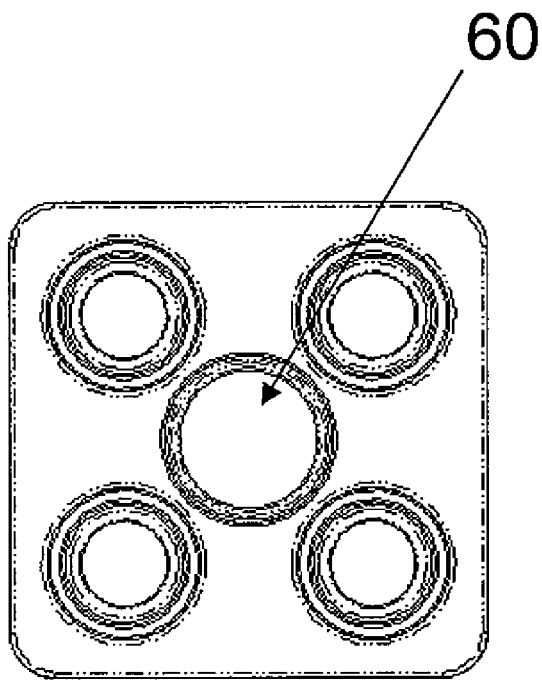
Figure 8D:
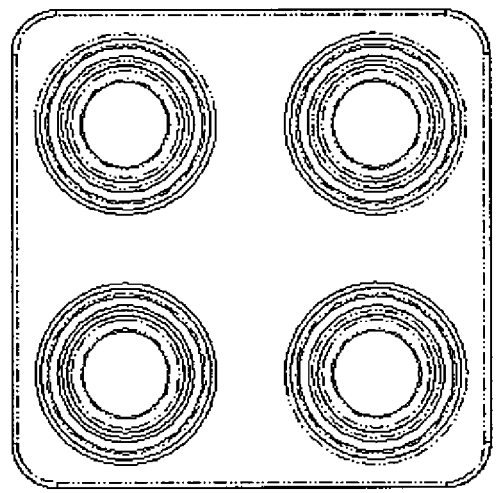

FIGS. 8A-8D depict additional embodiments of seal components. As shown in FIG. 8C, certain seal plates define a central opening 60. In certain embodiments, this central opening 60 may define a portion of a bolt shaft configured to receive a rotating cam or an assembly bolt, both of which are described below. Alternatively, certain seal plate embodiments such as that depicted in FIG. 8D have no central opening.

In one embodiment, a seal component is made out of biocompatible, compliant thermoset or thermoplastic polymer, such as, but not limited to, a silicone rubber. Alternatively, the seal component may be made of any known compliant biocompatible material that may be used for providing a seal in a medical device.

Figure 9:
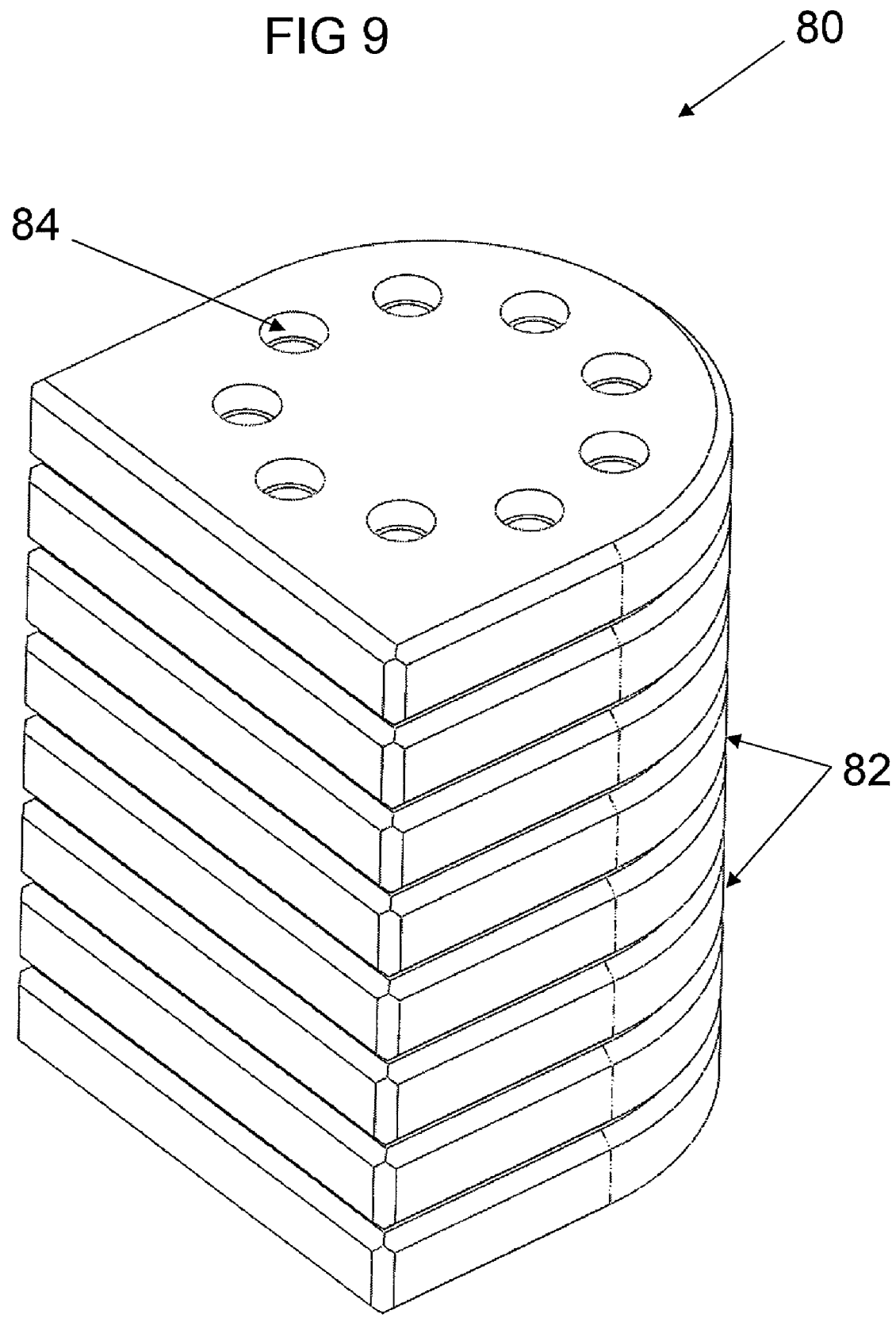
FIG. 9 depicts an alternative embodiment of an electrical connection apparatus having stackable connector blocks.

FIG. 9 depicts an alternative embodiment of a connector apparatus 80 having stackable connector blocks 82. In this embodiment, each block 82 has a D-shaped configuration and defines nine pin receiving portions 84. Alternatively, the block 82 may define any number of pin receiving portions that will fit on the block 82 and operate to provide an electrical connection. It is understood that the blocks 82 and pin receiving portions 84 may also have any other configuration. That is, the blocks 82 might be formed in another shape and/or the pin receiving portions 84 might be arranged in any other configuration on the blocks 82. It is also understood that any of these alternative embodiments could incorporate any of the various components described herein.

In a further alternative, the stackable blocks are secured in another fashion. That is, according to one embodiment, in the absence of the cam assembly, the blocks may be secured via a bolt that is disposed through a central hole in each of the stackable blocks 12 and the insertion end block 14. One example of such a central hole 60 is depicted in FIG. 8C. According to one embodiment, the bolt may be secured to the end block 16 via a mating feature. For example, the bolt may have a threaded end that mates with a threaded hole in the end block 16. Alternatively, any known components for securing such a bolt to an end block may be used. The bolt may be fabricated from a high strength biocompatible material such as stainless steel, a titanium alloy, a Co—Cr alloy such as MP35N, an Inconel alloy, or any other known high strength biocompatible material. In one implementation, the proximal portion of the bolt has a drive mechanism to allow for proper tightening on the assembly and may also have an over cap to minimize potential exposed surface crevices after assembly. In one embodiment, the bolt is the only feature for securing the blocks together. Alternatively, the bolt may be used in conjunction with the external clip 110.

FIG. 10 depicts an electrical connection apparatus 100, according to another embodiment. This apparatus 100 provides for easy insertion and removal of contact pins. The apparatus 100 has four pin receiving portions 104 defined within the blocks 102 of the apparatus 100. As discussed above with the embodiment depicted in FIG. 1, the pin receiving portions 104 are disposed through almost the entire length of the device 100. A pin (not shown) may be inserted into each of the pin receiving portions 104 and once activated, will be placed in contact with each of the C-shaped contact points 108 (see FIG. 11A) as described below. As in the previous embodiment depicted in FIG. 1, each pin has internal wires or leads that are electrically connected to the circumferential contact areas of the pin, similar to areas 34 as shown in shown in FIG. 1.

FIG. 10 also depicts one embodiment for securing the stackable blocks 102. That is, the blocks 102 are secured with an external clip 110 that connects the end cap block 16 to the insertion end block 14. In one implementation, the clip 110 is a single U-shaped spring that has two ends. The first end is secured at a first attachment point 109 on the end block and the second end is secured at a second attachment point 111. The length of the U-shaped clip 110 runs along the outside of the device 100 and wraps around the other end block along a channel defined in the other end block, thereby securing the stackable blocks 102 together. Alternatively, the external clip 110 may be two C-shaped clips, each having a hook-like feature at each end of the clip. In this embodiment, there are two attachment points in each end block (instead of just one end block as shown in FIG. 10) such that one C-shaped clip 110 is disposed on one exterior side of the connector 100 and the other C-shaped clip is disposed on the opposite side and both are attached to the end blocks with the hook feature.

Figure 11A:
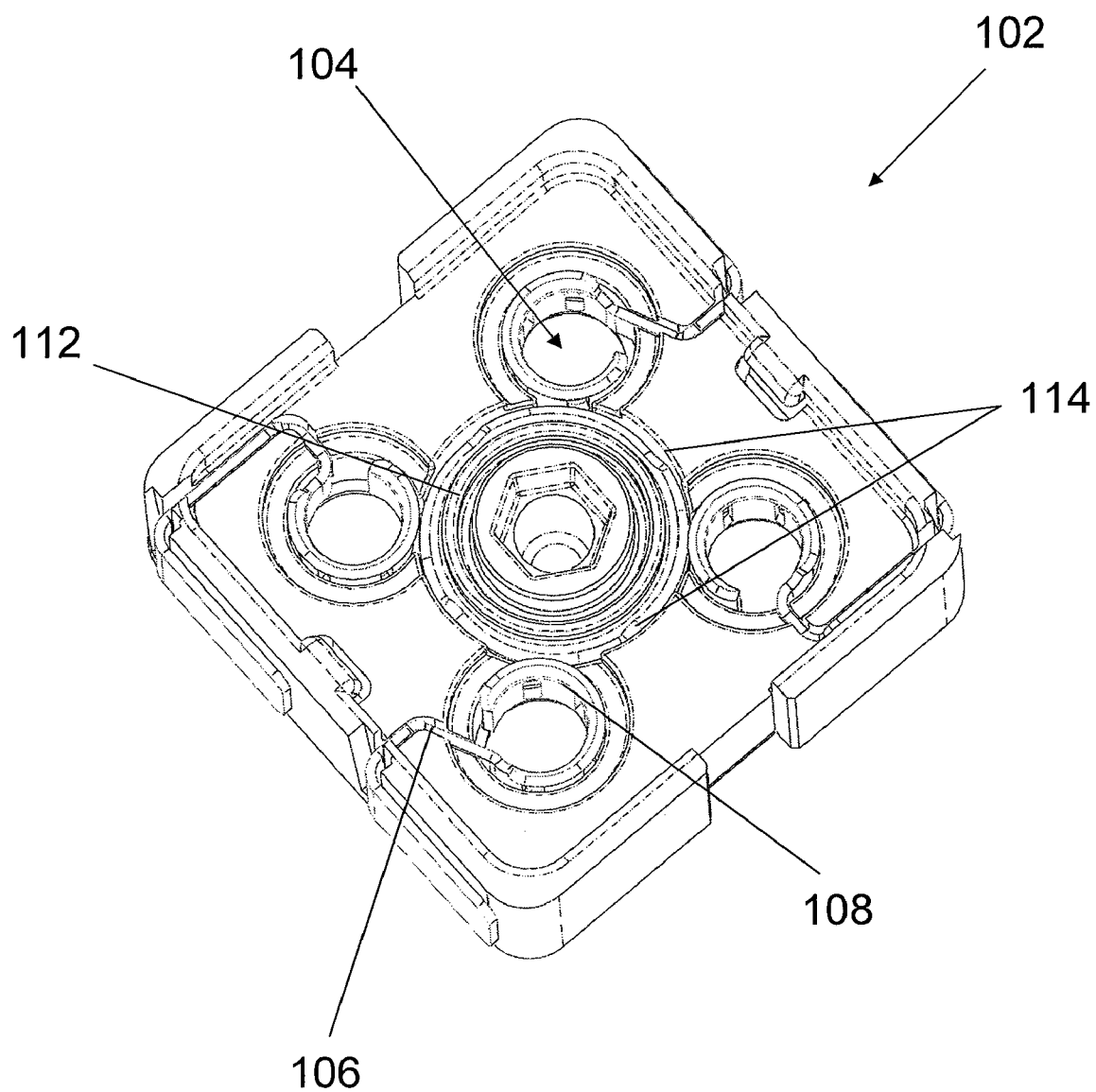
FIGS. 11A-C depict a block of the apparatus depicted in FIG. 10.

FIG. 11A depicts a block 102 of the apparatus depicted in FIG. 10. Like the blocks depicted in FIGS. 4A and 4B, block 102 has C-shaped contact portions 108 disposed within pin receiving portions 104. However, the C-shaped contact portions 108 in this embodiment differ from the C-shaped contact portions 28 described above with respect to FIGS. 3, 4A, and 4B. More specifically, the C-shaped contact portions 108 do not have an unconstrained diameter that is smaller than the OD of the pin. To the contrary, the natural configuration of the C-shaped contact portions 108 in this embodiment have a diameter that is greater than the OD of the pin.

Figure 12A:
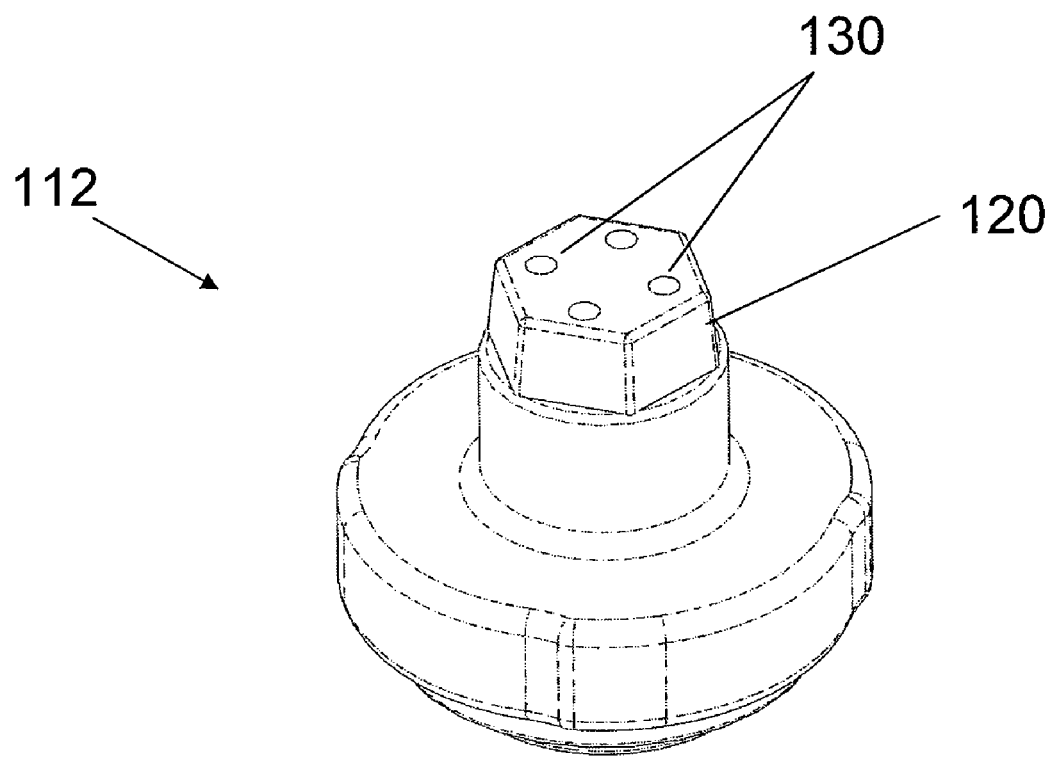
FIGS. 12A-B depict a first and second sides of a cam component.
Figure 12B:
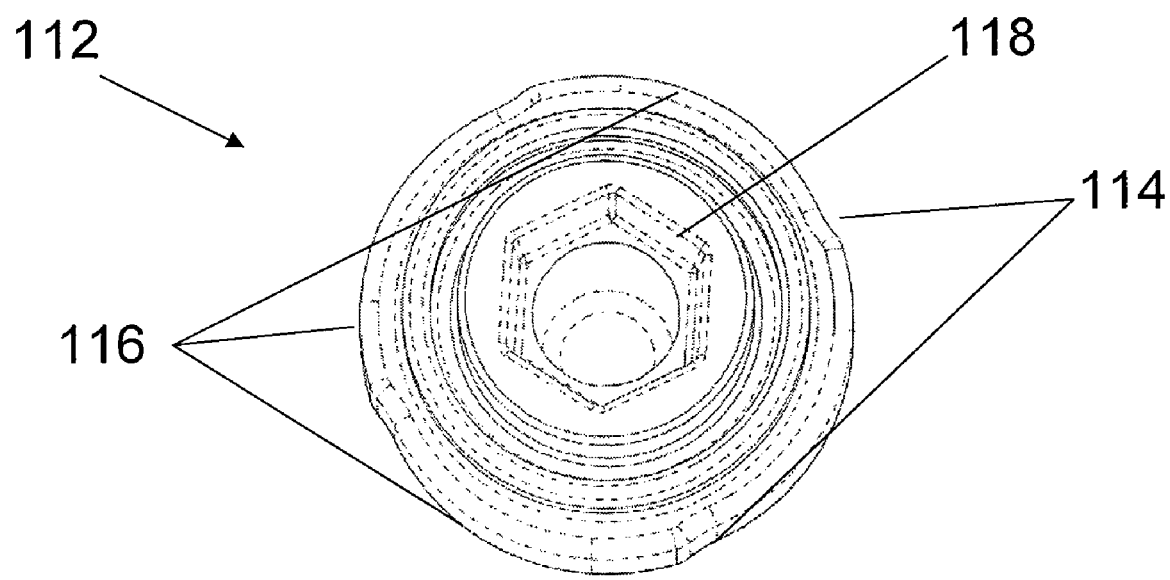

In addition, the block 102 has a cam component 112 disposed in a central portion of the block 102 such that the cam component 112 is in contact with each of the pin receiving portions 104. The cam component 112, which is depicted in further detail according to one embodiment in FIGS. 12A and 12B (which depict both sides of a cam component 112), has four indentations 114 and four contact portions 116 around the circumference of the component 112. In addition, the component 112 has a drive receiving component 118 on one side as shown in FIG. 12B and drive component 120 on the other side as shown in FIG. 12A. According to one embodiment, the drive receiving component 118 is an inset hexagon 118 and the drive component 120 is a coupleable hexagon drive component 120.

Each block 102 in this embodiment has a similar cam component 112 such that when the blocks 102 are connected to each other, the drive components 120 of each cam component 112 are inserted into the adjacent drive receiving component 118 on the adjacent block 102, thereby resulting in each of the cam components 112 in each of the blocks 102 being connected. In this embodiment, the connected cam components 112 may be turned using a tool 122 depicted in FIG. 13, e.g., a wrench such as a torque wrench.

Figure 13:
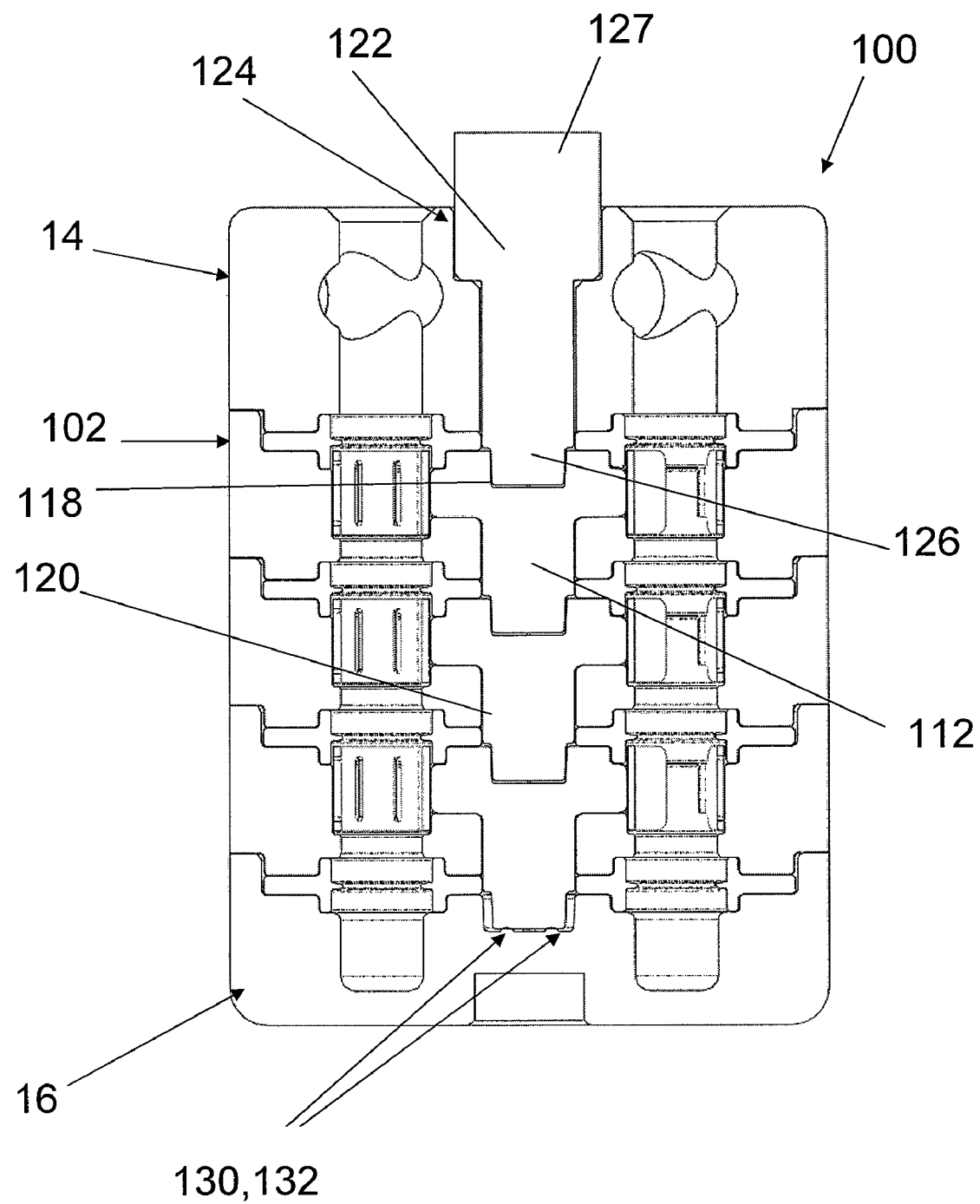
FIG. 13 depicts a cross-sectional view of the an electrical connection apparatus according to an alternative configuration.

According to the electrical connection apparatus 100 depicted in FIG. 13, the tool 122 is inserted through a central hole 124 defined in the end block 14 and positioned into the drive receiving component 118 of the cam component 112 of the block 102 connected to the end block 14, whereby the tool 122 may be used to turn the connected cam components 112.

In one embodiment, the tool 122 has on its distal end 126 (the end that contacts the drive receiving component 118) certain features that may improve torque transmission. According to one embodiment, the feature may be a shaped end (such as a hexagonal shape, for instance) that is mateable with the drive receiving feature 118 of the cam 112. Additionally, in one implementation, the proximal end 127 of the tool 122 may have screw drive features (such as slots, hex, torx, etc.), external knurling, increased circumference flange, or any other known features for improving torque transmission. In one implementation, the proximal end 127 of tool 122 is configured as a hex driver.

Figures 11B, 11C:
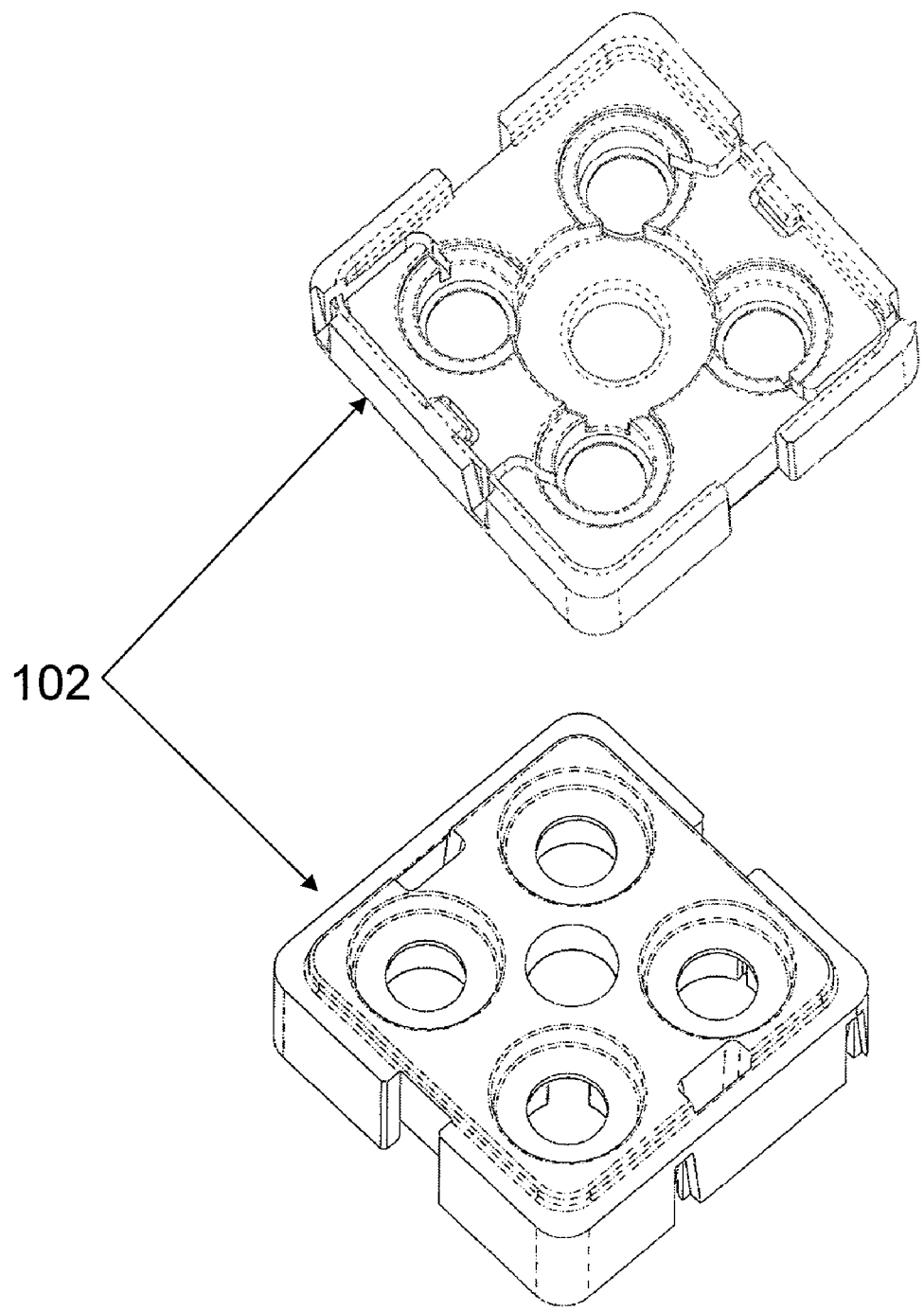

As best depicted in both FIGS. 11A-C, it is understood that the configuration of blocks 102 is slightly different from the blocks depicted in FIGS. 4A and 4B. That is, the slots in blocks 102 have a different configuration to accommodate the slightly different configuration of the electrical connection contacts. According to one embodiment, this configuration allows for a central hole defined in each of the assembly blocks 102.

In use, the cam component 112 provides for the easy insertion and removal of the pins. That is, when the cam component 112 is rotatably disposed such that the four indentations 114 are adjacent to the pin receiving portions 104 (the "insertion position"), each C-shaped contact portion 108 is disposed at its largest diameter, which is greater than the OD of a pin. Thus, when the cam component 112 is in the insertion position, a pin may easily be inserted into or removed from a pin receiving portion 104 while experiencing little or no frictional contact with the C-shaped contact portion 108. Thus, the pin may be inserted or removed with little or no force.

In contrast, when the cam component 112 is rotatably disposed such that the four contact portions 116 are adjacent to the pin receiving portions 104 and in contact with the C-shaped contact portions 108 (the "contact position"), each C-shaped contact portion 108 is urged into contact with the pin by the force of the contact portion 116 of the cam component 112, thereby resulting in electrical contact between the C-shaped contact portion 108 and the pin. An example of the contact position is depicted in FIG. 11A. In one embodiment, the C-shaped contact portion 108 is in electrical contact with the circumferential contact area of the pin similar to the contact area 34 depicted in FIG. 1.

Thus, the tool 122 may be used to turn the connected cam components 112, thereby moving the C-shaped contacts 108 between the insertion position and the contact position. That is, the tool 122 may be used to turn the cam components 112 such that the contact portions 116 are positioned in contact with the C-shaped contacts 108, thereby urging them into contact with the pins. In addition to establishing a stable electrical contact interface between the C-shaped contacts 108 and the pin, the pressure of the C-shaped contacts 108 against the pin acts to prevent movement of the pin or otherwise secure the pin in its position within the pin receiving portion 104.

Further, the tool 122 may be used to turn the cam component 112 such that the four indentations 114 are in contact with the four C-shaped contacts 108, thereby allowing each C-shaped contact 108 to expand and to return to the insertion/withdrawal position.

In certain embodiments, after the cams 112 are set to the appropriate position, the tool 122 may be removed and replaced with a lower profile cap. Alternatively, no cap is provided.

According to one implementation, the combined force of the C-shaped contacts 108 in contact with the pin creates a sufficiently large mechanical force on the pin such that the pin is not easily dislodged or otherwise disconnected via physical movement of the device 100 or pin. As such, the device 100 may withstand outside physical forces, including shaking, twisting, and/or other such forces, without disrupting the connection between the pins and the contact portions 108 as a result of the stable configuration of the contact adjustment component 112 and contact portions 108. As an example, this stability may, in some embodiments, allow a patient requiring such a device 100 to be more physically active than is possible with known devices. In another embodiment, the apparatus 100 may also have a mechanical fastening port (not shown) similar to that described above with respect to FIG. 1, thereby providing further stability.

In the embodiment shown in FIG. 13, an apparatus may provide a tactile response to rotation of the cam component 112 such that a user may properly position the cam component 112. In one embodiment, the tactile response is provided by mated detent features disposed on the drive component 120 of the cam component 112 as shown in FIG. 12A and on the portion of that end block 16 that contacts the cam component 112 as shown in FIG. 13. More specifically, the drive component 120 has female detent features 130 shaped as hemispheres formed into the end of the component 120. Further, the end block 16 has male detent features 132 shaped as hemispheres that may mate with the female detent features 130. In use, as the cam component 112 is turned, the user may feel the mating and unmating of the detent features and thereby may easily determine the position of the cam component 112. According to one embodiment, the detent features 130, 132 are positioned such that the features mate when the cam component 112 is positioned in the contact position, such that the tactile response of the detent features 130, 132 mating indicates to the user that the cam component 112 is in the contact position.

In an alternative embodiment, a tactile response is achieved through a set of small indentations (not shown) disposed on the contact portions 116 of the cam component 112. These indentations are much smaller and shallower than the indentations 114 and are placed at the optimal contact points 116 on the cam component 112. These indentations provide a tactile response to the user, indicating that the cam component 112 is in the contact position.

In a further embodiment, a visual method of positioning the cam component 112 is provided. In this embodiment, alignment markers are placed on the end block 14 and the top of the cam tool 122.

Figure 14A:
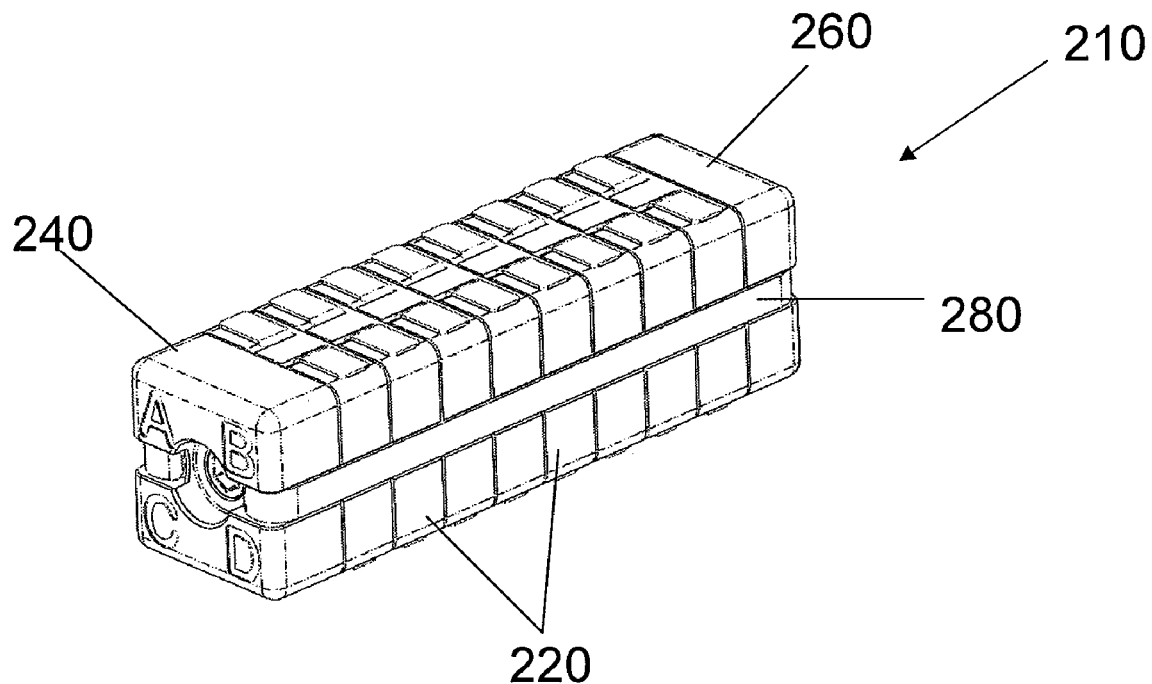
FIGS. 14A-B depict a first and second perspective view of another electrical connection apparatus according to certain implementations.
Figure 14B:
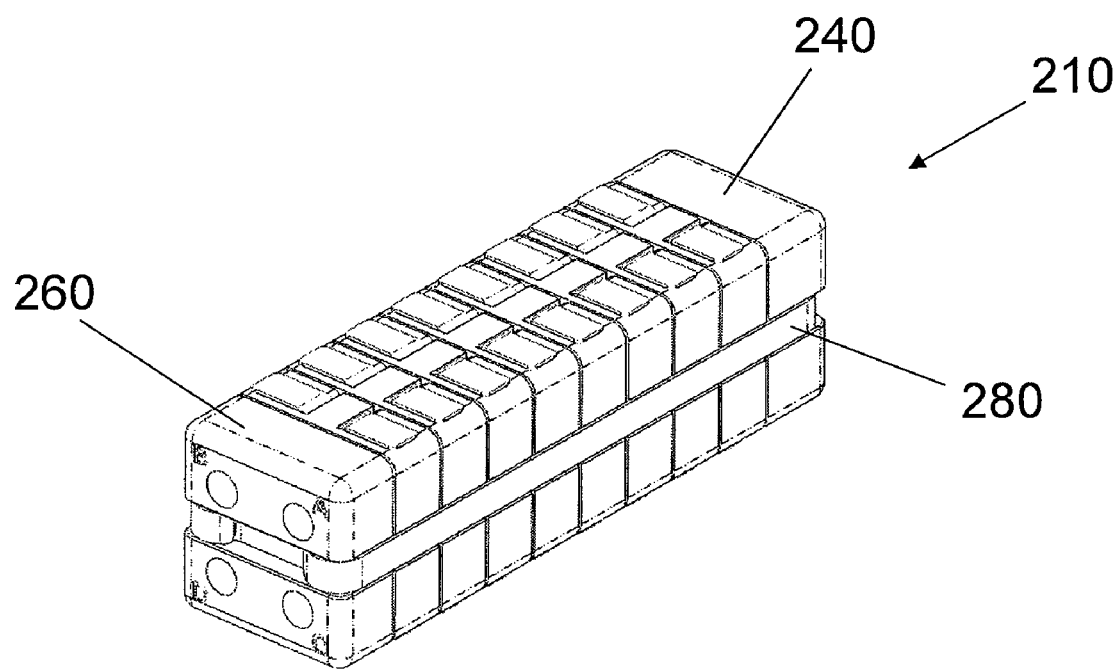

FIGS. 14A-B depict a first and second perspective view of another electrical connection apparatus 210, according to certain implementations. The electrical connection apparatus 210 includes stackable blocks 220 arranged between end blocks 240, 260. The assembly of blocks 220, 240 and 260 may be held together by external spring clip 280 or by a U-shaped clip (not shown) with the terminal ends of the U-shaped clip terminating at end block 240. Electrical connection apparatus 210 may connect two implantable components, e.g., leads and a medical device, in the manner discussed above in relation to the electrical connection apparatus 10 of FIG. 1. However, according to the presently described implementation, the electrical connection apparatus 210 is configured so that cam action is initiated from one end, e.g., the end corresponding to end block 240, and pins enter from another end of apparatus 210, e.g., the end corresponding to end block 260. This embodiment may provide certain advantages because, due to the small allowable space for active implantable devices and the small sizing of the electrical connectors, placing leads at one end of the device and rotating the cam at the opposite end may reduce the chance of entanglement between the leads and the rotating mechanism, hands, tool, torque wrench, etc., during manual rotation or operation of the cam.

FIGS. 15A-F depict perspective views of a first and second side of a first end block 240, a stackable block 220 and a second end block 260 of apparatus 210 shown in FIGS. 14A-B.

In FIGS. 15A-B, end block 240 is configured with grooves 241 on opposite sides of the block for accommodating external clip 280, an opening 242, which provides access to a cam or other adjustment component (not shown) situated in an adjacent stackable block 220, and receivers 243 for receiving retaining clips 222 arranged on stackable block 220 (shown in FIG. 15C). End block 240 serves as an access point for accessing a cam or other adjustment component arranged on the interior of the assembled apparatus 210 and may have a configuration similar to insertion end block 14 of FIG. 1, except that end block 240 does not include the pin receiving portions described in relation to FIG. 1.

FIGS. 15C-D depict perspective views of a first and second side of a stackable block 220. In FIGS. 15C-D, block 220 includes grooves 221, retaining clip 222, receivers 222' for retaining clips 222, knife edges 223, slots 224, potting pockets 225, cam receiving portion 226, cam detents 227, cam hard stops 228 and pin receiving portions 229. Grooves 221 on opposite sides of the block accommodate spring clip 280 and may facilitate maintaining the desired positioning of spring clip 280 on the assembled apparatus 210. Retaining clips 222 arranged near the periphery of an interior facing portion of block 220 may facilitate holding seals 250 in place (See FIG. 21A) and may aid in assembly of adjacent blocks, e.g., adjacent end blocks 240, 260 or other stackable blocks 220. For example, during assembly, retaining clips 222 may engage with receivers 222' arranged near the periphery of an interior facing portion of another block 220 or from receivers 243 arranged near the periphery of an interior facing portion of an adjacent end block 240. Knife edges 223 provided on stackable blocks 220 may facilitate providing a seal between seal plate 250 and stackable blocks 220.

Each stackable block includes four slots 224 for providing an electrical connection contact (not shown) access to the exterior of the block 220. Four potting pockets 225 are arranged in an area proximate the slot 224 and may accommodate an epoxy or other polymeric resin, which may seal slots 224 and prevent moisture ingress to the interior of apparatus 210. Cam receiving portion 226 is defined by interior walls of stackable block 220 and is configured to receive a cam (not shown) or other adjustment component and includes cam hard stops 228 that cooperate with the cam 330 and serve as stop points for the cam rotating from a locking or contact to an unlocking or insertion position. Cam detents 227 are arranged adjacent the cam hard stops 228 and serve as an indicator to a user rotating the cam that the cam has reached a locking or contact position or an unlocking or insertion position. Four pin receiving portions 229 are each configured to accept a pin (not shown) and are defined by interior walls of stackable block 220.

FIGS. 15E-F depict perspective views of a first and second side of a second end block 260, which may be configured similar to end cap block 16 described in relation to FIG. 1, except that end block 260 may include pin receiving portions and/or fastening ports similar to those provided in insertion end block 14. End block 260 also includes a groove 261 for accommodating external spring clip 280 or a U-shaped spring that would traverse exterior of the second end block along the length of the groove.

Figure 16A:
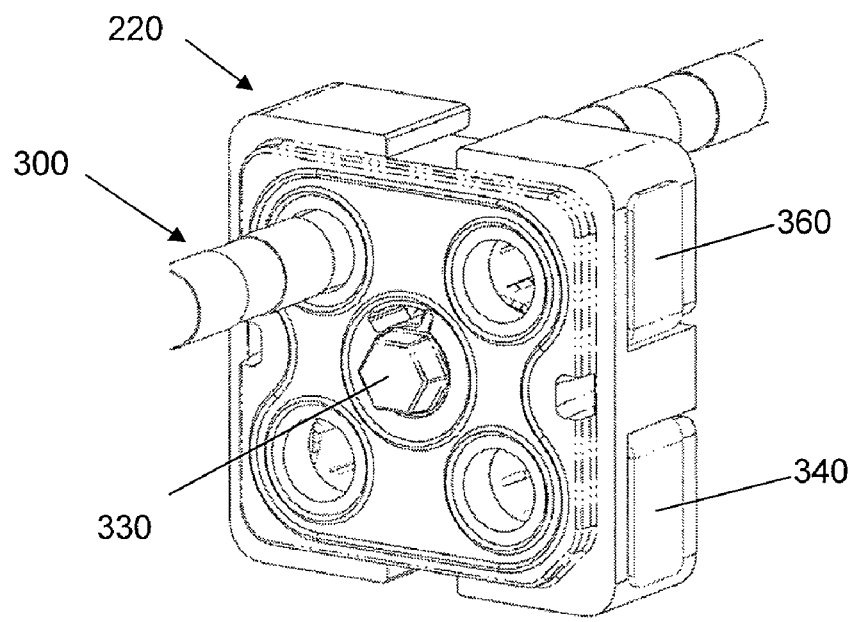
FIGS. 16A-B depict perspective views of a first and second side of a stackable block with a segmented contacting pin in place.
Figure 16B:
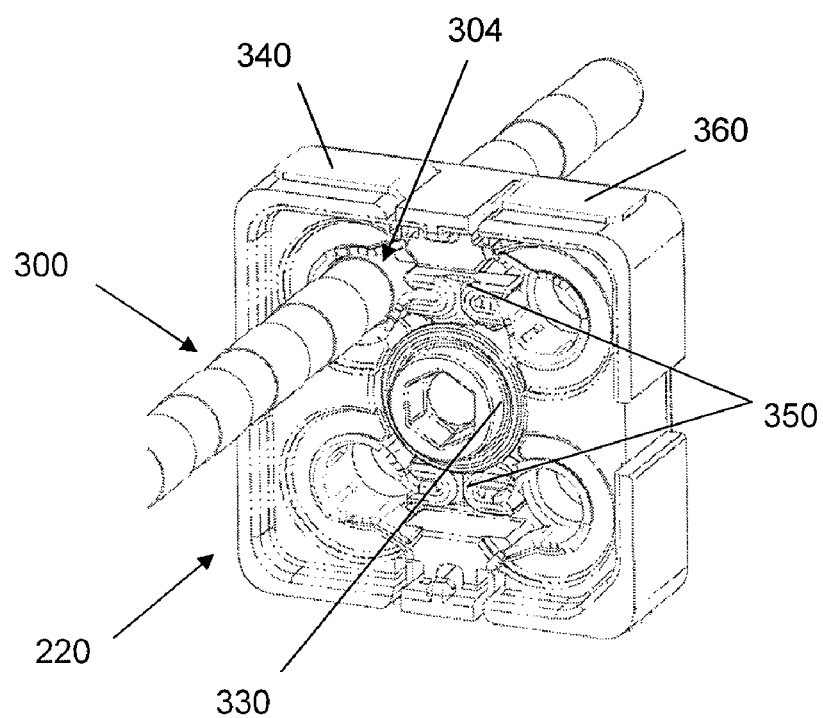

FIGS. 16A-B depict perspective views of a first and second side of the stackable block 220 with a pin 300 inserted through the block. FIG. 16A depicts a drive component of cam 330 in an insertion position. FIG. 16B depicts the assembly from the back side and the cam 330 with the drive receiving component is set in the open or initial insertion position.

Figure 17A:
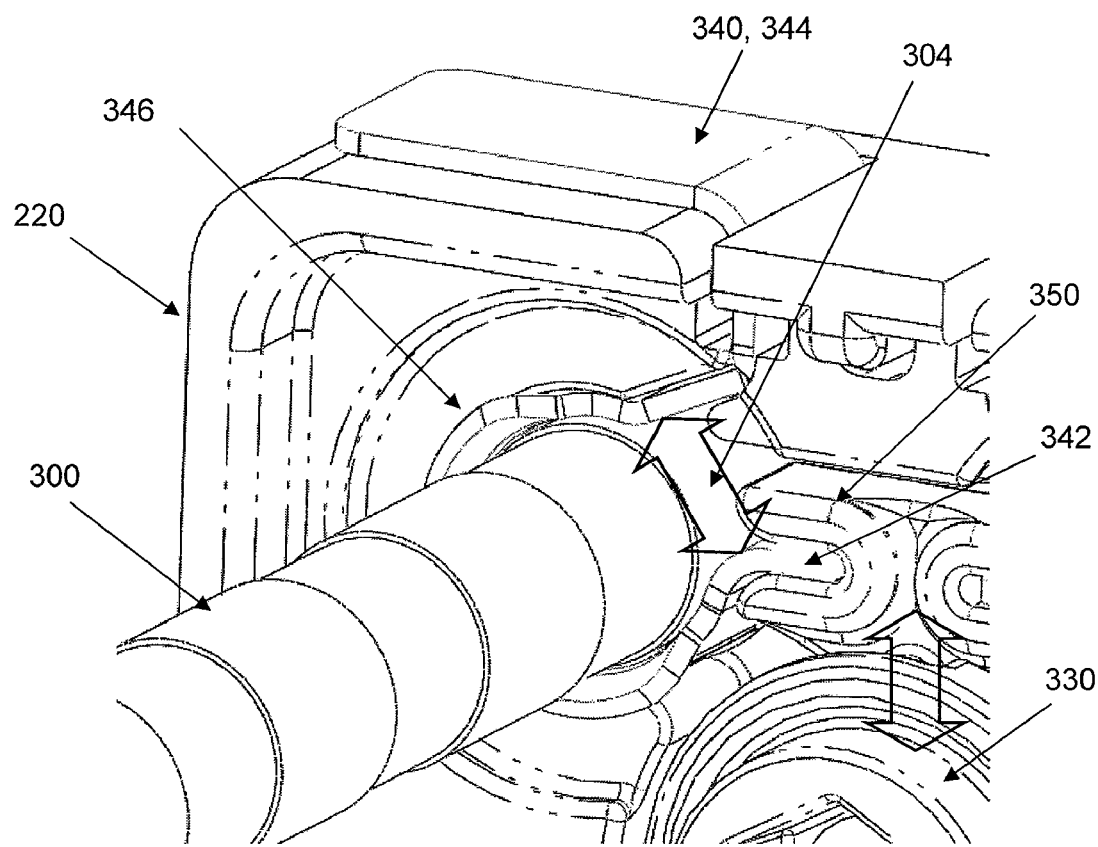
FIGS. 17A-B depict perspective views of the slider and contact in both the insertion and contact position relative to the pin.

FIG. 17A depicts one of the contact assemblies in the unlocked position. The cam 330 is loosely coupled to a slider 350, which is mechanically engaged to an electrical connection contact 340 via a tab 342 (see FIG. 19A). In the unlocked position, slider 350 is in a lowered position relative to the periphery of stackable block 220 and loosely engaged with electrical connection contact 340. Electrical connection contact 340 is in a relaxed state, and as a result, pin 300 arranged in block 220 may be slidable through the C-shaped connection 346 in the contact 340. Thus, in FIG. 17A, the cam 330, slider 350 and tab 342 are in an insertion position, and a pin may be inserted into or removed from a pin receiving portion 229 while experiencing little or no frictional contact with the C-shaped contact portion 346, resulting in the pin being insertable or removable with little or with zero insertion force.

Figure 17B:
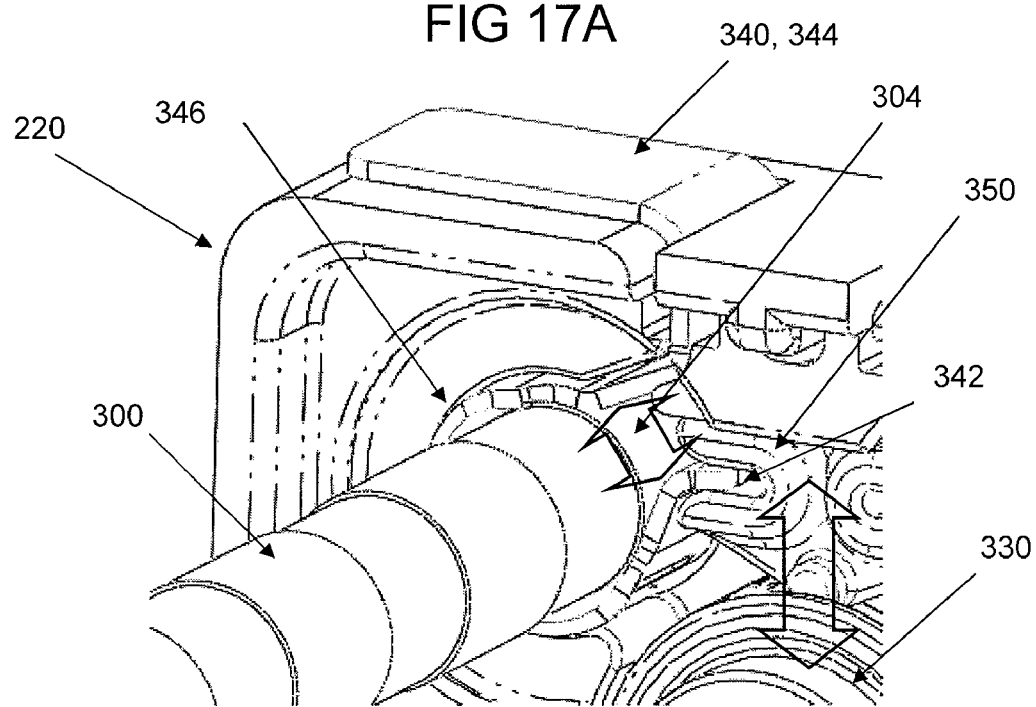

In FIG. 17B, a first side of the contact assembly is shown in its locked position. Cam 330 has raised the position of slider 350 and C-shaped contact portion 346 is clinched around pin 300 at an electrically-isolated circumferential contact 304. As a result, when cam 330 is in a locked position, pin 300 is locked into position about its circumferential contact 304 by the reduction of the circumference of the C-shaped portion of electrical C-shaped contact 346. This action completes the electrical path from the external contacts 344 through the C-shaped contact 346 to the isolated pin contact 304 to the internal pin lead 30 (see FIG. 1). When four pins 300 are provided in apparatus 210, each slider 350 is responsible for raising the position of two tabs 342, 362 (see FIGS. 19A and B), which in turns clinches two of the four pins 300. Providing sliders 350 that engage with tabs 342, 362 to cause the C-shaped contacts 346 to tighten around and couple to pins 300 in response to cam action, according to the present implementation, may reduce or prevent buckling of the C-shaped portion 346, 366 of the electrical connection contacts 340, 360.

According to FIG. 17B, in addition to establishing a stable electrical contact interface between the C-shaped contacts 346 and the pin 300, the pressure of the C-shaped contacts 346 against pin 300, due to the positioning of slider 350 in a contact position, may prevent movement of the pin or secure the pin in its position within the pin receiving portion 229. The force of the C-shaped contact 346 in contact with the pin may provide a sufficiently large mechanical force on the pin such that the pin may not be dislodged or dislodged easily, or otherwise disconnected via physical movement of the device 210 or pin 300. Thus, the device 210 may withstand outside physical forces, including shaking, twisting, and/or other such forces, without disrupting the connection between the pins and the contact portions 346 as a result of the stable configuration of the cam 330, slider 350 and tab 342.

Figure 18A:
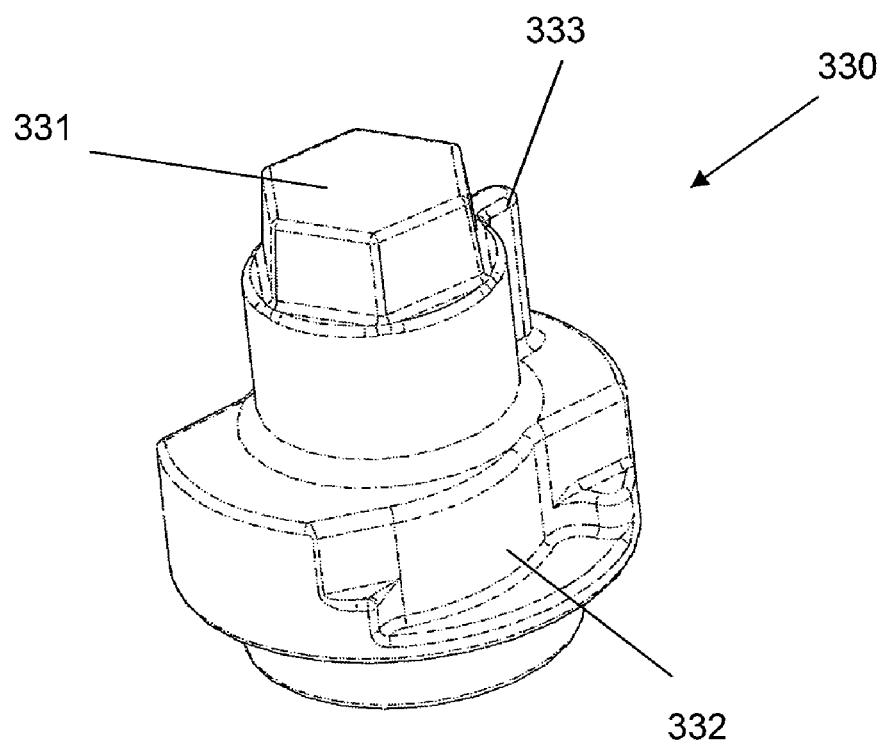
FIGS. 18A-B depict perspective views of a first and second side of a cam according to certain implementations.
Figure 18B:
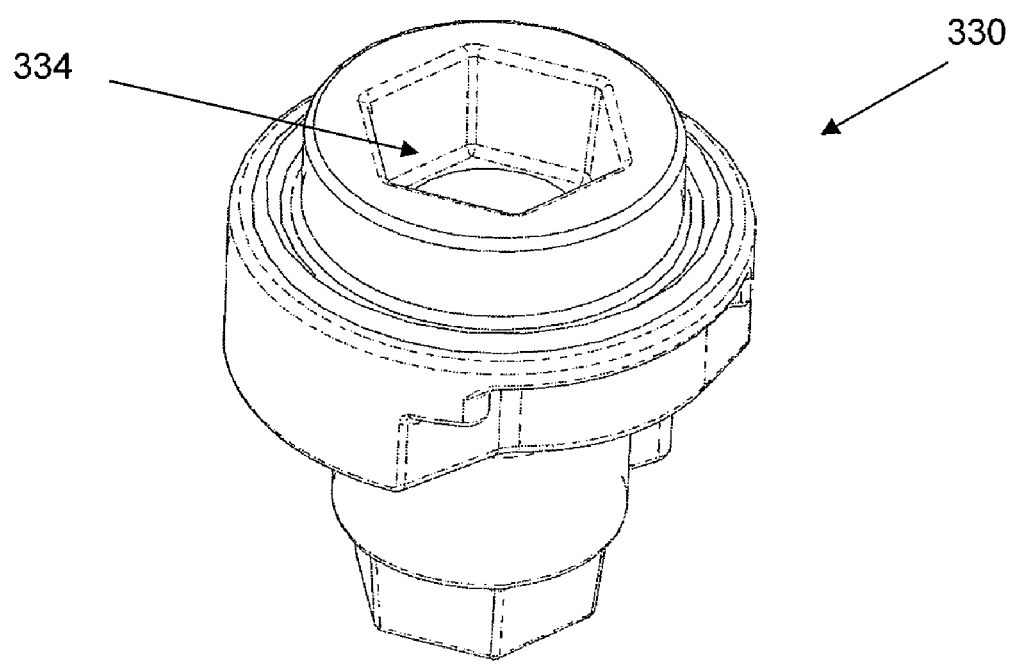

FIGS. 18A-B depict perspective views of a first and second side of cam 330. Cam 330 includes a drive component 331, eccentric paths 332 for sliders 350, detent feature 333 and a drive receiving component 334. In FIG. 18A, the drive component 331 having a tapered hexagonal male portion is configured such that it fits into an adjacent cam by way of a complementary drive receiving component 334 having a tapered hexagonal female receiving configuration. When cam 330 is arranged in block 220, the drive component 331 protrudes beyond the an exterior surface of block 220, see e.g., FIGS. 16A and 17A. Eccentric paths 332 for slider 350 may be configured so that when cam 330 is arranged in block 220, eccentric paths 332 loosely couple to the sliders 350 when in an insertion or unlocked position, and moves sliders 350 up or down when in a contact or locked position. Detent feature 333 engages with cam detents 227 of block 220 when cam 330 is moved to either a locked or an unlocked position. When detent feature 333 reaches one of the cam detents 227, a user exerting torque, e.g., by way of a tool such as a wrench or a torque wrench, on the cam assembly may feel detent feature 333 engage with the cam detent. Where a user continues to exert torque on the cam assembly after the detent feature 333 engages with cam detent, detent feature 333 may abut an adjacent cam of the pair of cam hard stops 228 provided on block 220 preventing cams from further rotational movement. In use, cams 330 from adjacent blocks 220 interlock via the drive and drive receiving components 331, 334, respectively. Accordingly, actuation of a cam 330 arranged in a stackable block 220 adjacent to end block 240 results in actuation of each of the cams 330 arranged in the electrical connection apparatus 210. Furthermore, because detents 227 and hard stops 228 in stackable block 220 cooperate with cam 330, initiating cam action with a torque wrench may provide for precise engagement and rotation of cams 330 within electrical connection apparatus 110.

FIGS. 19A-B depict perspective views of electrical connection contact 340, 360 for use on a left and a right side of the stackable block 220. FIGS. 20A-B depict perspective views of a first and second side of a slider 350 for use with the stackable block 220 and include recesses 351 and 352 for engaging with electrical connection contact 340, 360. According to certain implementations, sliders 350 may be constructed of plastic, ceramic, other insulating material, or may be coated with an insulating material.

With reference to FIG. 19A, a left side electrical connection contact 340 includes tab 342 for engaging with slider recess 351, exterior contact portion 344 for contacting an external device and for aligning along an exterior length of the stackable block 220, and C-shaped interior contact portion 346 for aligning with pin receiving portion 229 and for contacting pin 300. In FIG. 19B, a right side electrical connection contact 360 includes tab 362 configured for engaging with slider recess 351, exterior contact portion 364 for contacting an external device, and C-shaped interior contact portion 366 for aligning with pin receiving portion 229 and contacting pin 300. Tab 342, 362 provides slider recess 351 with a desirable length of the electrical connection contact 340, 360 such that the contact may be moved from an insertion to a contact position as a result of an upward or downward movement of the slider 350. Electrical connection contacts 340, 360 may also include features described above in relation to the electrical connection contacts of FIGS. 3A-B, 5A-G and 11.

Figures 21A, 21B:
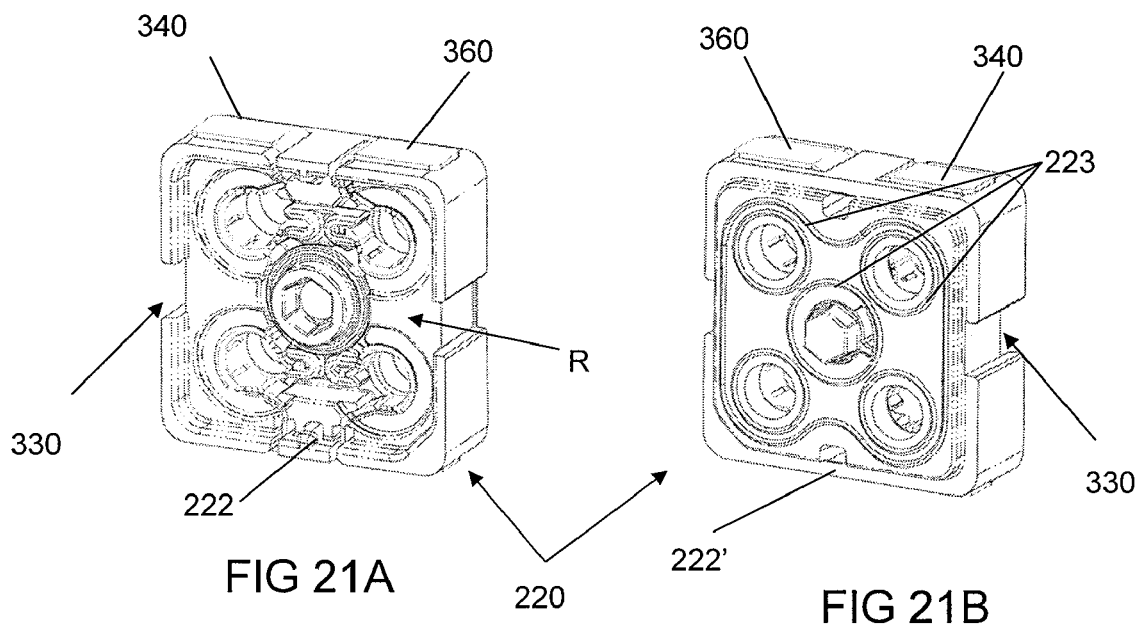
FIGS. 21A-B depict perspective views of a first and second side of the stackable block with a seal plate.
Figures 22A, 22B:
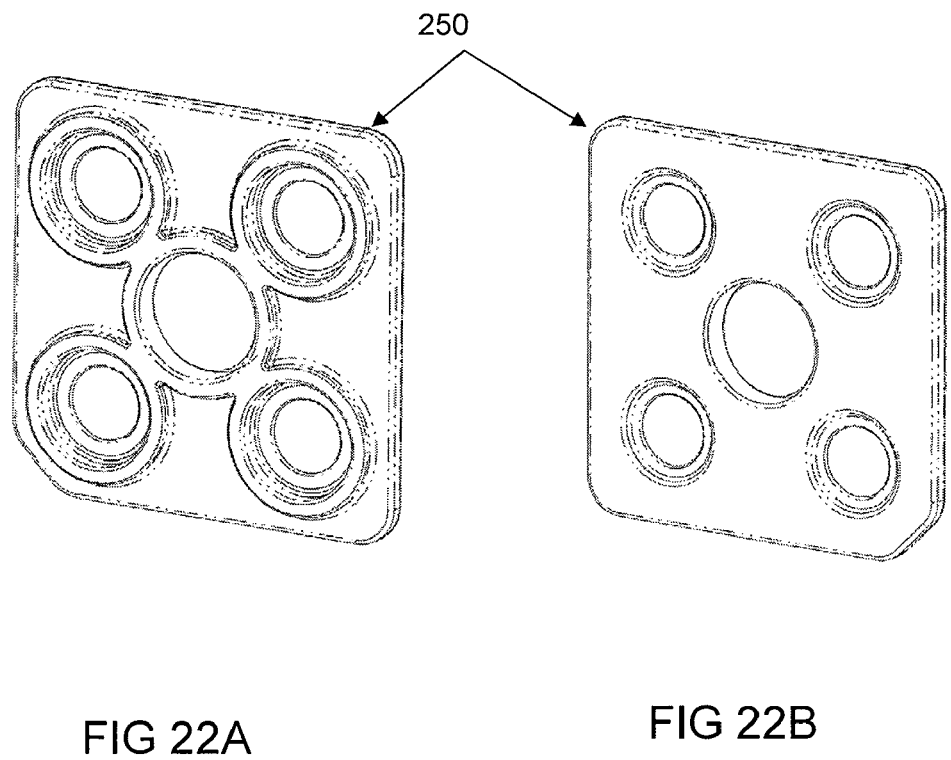
FIGS. 22A-B depict perspective views of a first and second side of the seal plate depicted in FIGS. 21A-B.

FIGS. 21A-B depict perspective views of a first and second side of the stackable block 220. FIGS. 22A-B depict perspective views of a first and second side of a seal component 250, which may be arranged on stackable block 220 at a position corresponding to the recessed portion R of seal block 220 depicted in FIG. 21A. Assembled electrical connection apparatus 210 (FIGS. 14A-B) may be provided with a seal component 250 between each block, e.g. between end block 240 and stackable block 220, between stackable blocks 220, and between stackable block 220 and end block 260 in order to prevent biological fluids from contacting pins 300, for example. In addition, stackable blocks 220 associated with the presently described apparatus 210 include clips 222, which may facilitate holding seal component 250 in place as well as engage with receivers 222', as shown in FIG. 21B. Moreover, knife edges 223 provided on stackable block 220 in the areas corresponding to the cam receiving portion 226, pin receiving portions 229, and an area surrounding each of the cam and pin receiving portions. Knife edges 223 may mate with vertical seal portions provided on seal component, which are shown and described in relation to FIG. 7.

Figure 23A:
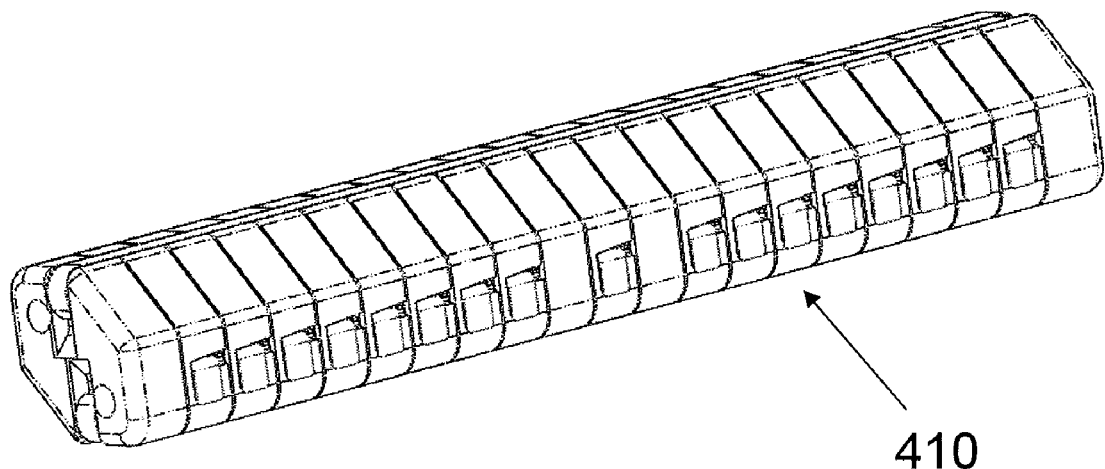
FIGS. 23A-B depict perspective views of a first and second perspective view of another electrical connection apparatus having a two pin configuration.
Figure 23B:
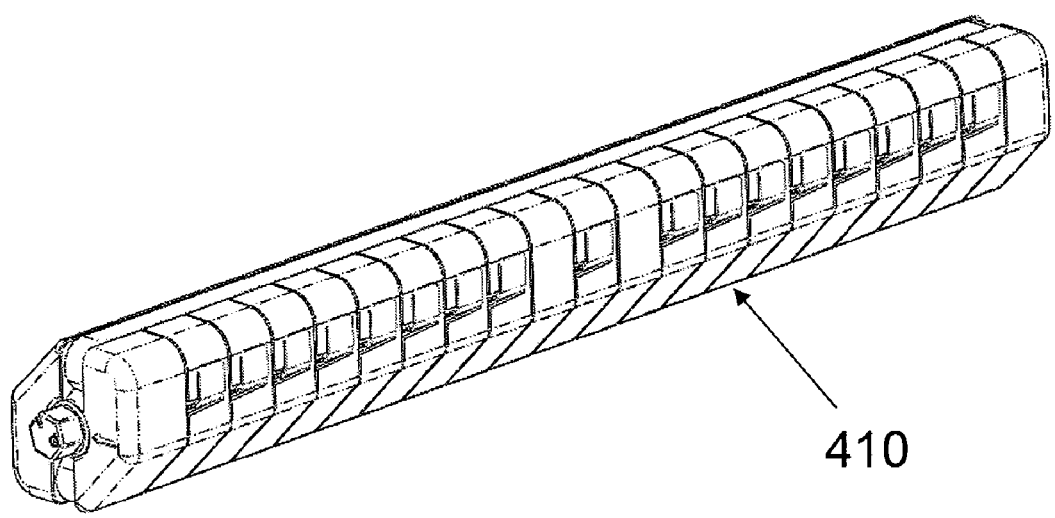

FIGS. 23A-B depict a first and second perspective view of another electrical connection apparatus 410 having a two pin configuration. Electrical connection apparatus 410 may otherwise be configured in a manner similar to that of electrical connection apparatus 10, 80, 100, and 210.

In certain implementations, all or a portion of electrical connection apparatus 10, 80, 100, 210 and 410 may be overmolded in silicone or another polymer in order to reduce or eliminate the chance of moisture ingress. In addition, in certain implementations, pin 20 and pin 300 may have a variety of diameters and configurations. For example, pins coupled to leads that deliver electrical pulses may be larger than pins coupled to sensing leads. Accordingly, the pin receiving portions of apparatus 10, 80, 100, 210 and/or 410 may be configured to accept a pin having a desirable cross-section or configuration.

Figure 24:
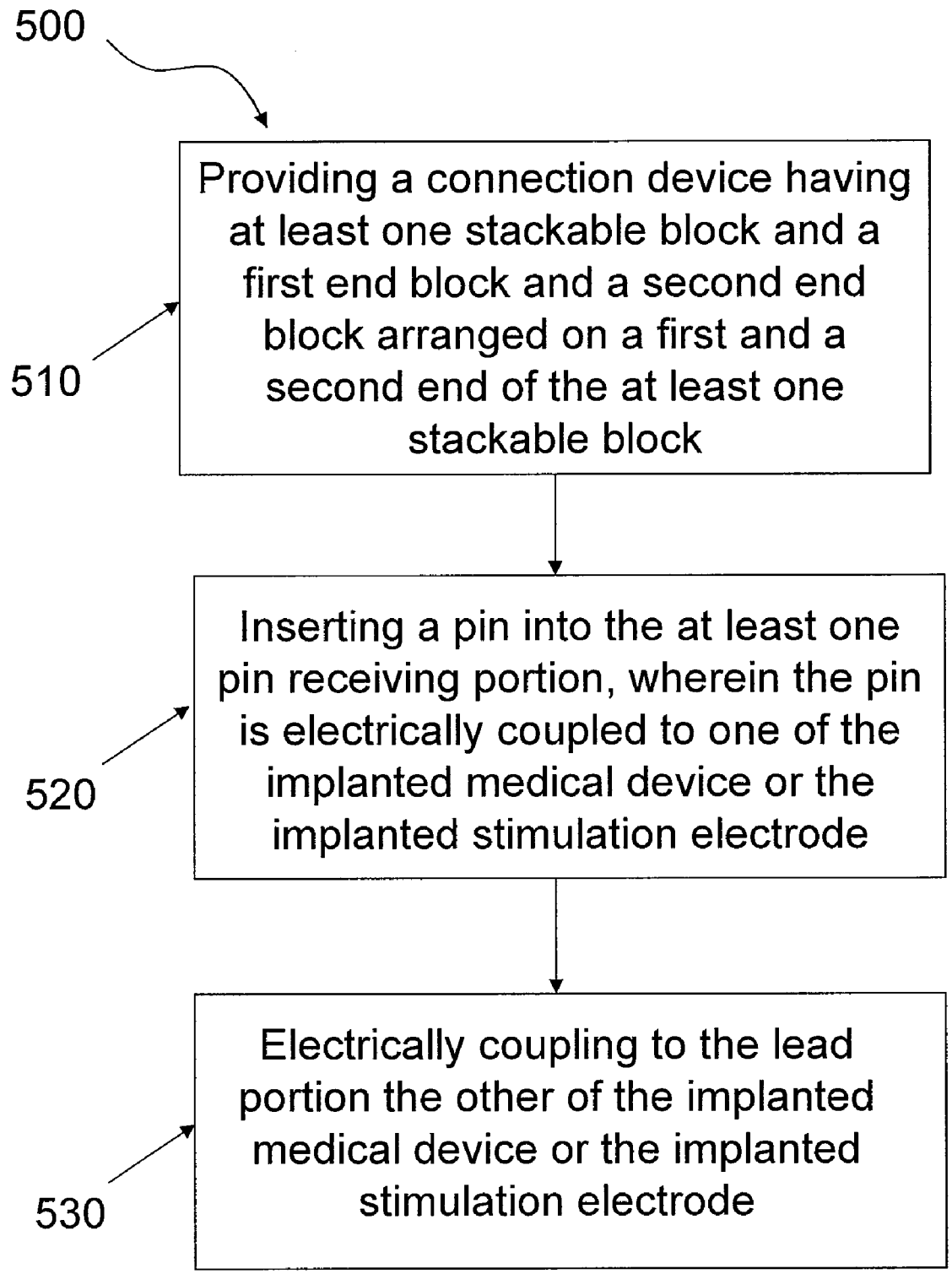
FIG. 24 is a flowchart of a method for electrically connecting an implanted medical device and an implanted stimulation electrode according to the present invention.

FIG. 24 is a flowchart of a method (500) for electrically connecting an implanted medical device and an implanted stimulation electrode according to the present invention. According to FIG. 24, method (500) includes providing (510) a connection device having at least one stackable block and a first end block and a second end block arranged on a first and a second end of the at least one stackable block, where each of the at least one stackable block includes at least one pin receiving portion, and at least one electrical connection contact. Method (500) also includes inserting (520) a pin into at least one pin receiving portion such that the pin is electrically coupled to an implanted medical device or to an implanted stimulation electrode, and electrically coupling (530) to the lead portion the other of the implanted medical device or the implanted stimulation electrode.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. An electrical connection apparatus comprising:
   (a) at least one stackable block, wherein each block is operably coupleable to another stackable block;
   (b) at least one pin receiving portion defined by an inner wall within the at least one stackable block;
   (c) at least one electrical connection contact comprising:
      (i) a C-shaped contact portion disposed within the at least one pin receiving portion, the C-shaped contact portion having elastic properties; and
      (ii) a lead portion disposed at a location exterior to the stackable block,
   wherein the C-shaped contact portion and the lead portion integrally form the at least one electrical connection contact; and
   (d) an adjustment component rotatably disposed in each of the at least one stackable blocks, the adjustment component configured to cause the C-shaped contact portion arranged in each of the at least one pin receiving portions to be urged between an insertion position and a contact position.

2. The apparatus of claim 1, wherein the electrical connection contact comprises a precious metal.

3. The apparatus of claim 1, further comprising at least one end block configured to couple with the at least one stackable block.

4. The apparatus of claim 3, further comprising an external clip configured to secure the end block and the least one stackable block.

5. The apparatus of claim 3, further comprising a bolt disposed through a central opening arranged in the at least one end block and each of the at least one stackable blocks, wherein the bolt is configured to secure the at least one end block and each of the at least one stackable blocks.

6. The apparatus of claim 1, further comprising a seal component associated with each of the at least one pin receiving portion, the seal component comprising a vertical seal portion and a horizontal seal portion.

7. The apparatus of claim 6, wherein the vertical seal portion comprises a first end and a second end, wherein the first end is configured to contact one of the at least one stackable blocks and the second is configured to contact another of the at least one stackable blocks.

8. The apparatus of claim 6, wherein the horizontal seal portion comprises a first end and a second end, wherein the first end is configured to contact a pin disposed in the pin receiving portion and the second end is configured to contact one of the at least one stackable blocks.

9. The apparatus of claim 8, whereby the horizontal seal creates a seal between two of the at least one stackable blocks.

10. The apparatus of claim 1, wherein the C-shaped contact portion has an unconstrained diameter that is larger than an outer diameter of a pin configured to be insertable into the at least one pin receiving portion.

11. The apparatus of claim 1, wherein the adjustment component comprises at least one cam contact portion operably coupleable with at least one of the C-shaped contact portion, wherein rotation of the adjustment component causes the at least one cam contact portion to urge the at least one C-shaped contact portion between the insertion position and the contact position.

12. The apparatus of claim 1, further comprising:
an electrical contact tab arranged on the terminal end of each of the C-shaped contact portions; and
at least one slider associated with the adjustment component and arranged in the stackable block, wherein the slider is configured to accept at least one of the electrical contact tabs, and wherein the adjustment component is configured to move up and down in response to rotation of the adjustment component which causes the tabs to move the C-shaped contact portion between the insertion position and the contact position.

13. The apparatus of claim 1, wherein the at least one stackable block comprises an adjustment component receiving portion configured to accept the adjustment component, wherein the adjustment component receiving portion comprises a first and a second hard stop, the first hard stop substantially corresponding to an insertion position of the adjustment component and the second hard stop substantially corresponding to a contact position of the adjustment component.

14. The apparatus of claim 13, wherein the adjustment component further comprises a drive component and a drive receiving component, wherein the drive receiving component is configured mate with another drive component of an adjacent adjustment component.

15. The apparatus of claim 14, further comprising a tool configured to engage with the drive receiving component in order to rotate the adjustment component between the insertion position and the contact position.

16. The apparatus of claim 1, further comprising a first end block comprising an adjustment component access portion defined by an inner wall, wherein the first end block is configured to couple to a first side of the at least one stackable block comprising an adjustment component.

17. The apparatus of claim 16, further comprising a second end block comprising at least one pin access portion defined by at least one inner wall, wherein the second end block is configured to couple to a second side of the at least one stackable block such that the at least one pin receiving portion defined by the inner wall within the at least one stackable block is positioned in an area corresponding to the area of the pin access portion of the second end block.

18. An electrical connection apparatus comprising:
(a) at least one stackable block, wherein each block is operably coupleable to another stackable block;
(b) at least one pin receiving portion defined by an inner wall within the at least one stackable block;
(c) at least one electrical connection contact comprising:
(i) a C-shaped contact portion disposed within the at least one pin receiving portion, the C-shaped contact portion having elastic properties; and
(ii) a lead portion disposed at a location exterior to the stackable block,
wherein the C-shaped contact portion and the lead portion integrally form the at least one electrical connection contact;
(d) at least one end block configured to couple with the at least one stackable block; and
(e) a bolt disposed through a central opening arranged in the at least one end block and each of the at least one stackable blocks, wherein the bolt is configured to secure the at least one end block and each of the at least one stackable blocks.

19. The apparatus of claim 18, wherein the C-shaped contact portion comprises an unconstrained diameter that is smaller than an outer diameter of a pin insertable into the at least one pin receiving portion.

20. The apparatus of claim 18, wherein the electrical connection contact comprises a precious metal.

21. An electrical connection apparatus comprising:
(a) at least one stackable block, wherein each block is operably coupleable to another stackable block;
(b) at least one pin receiving portion defined by an inner wall within the at least one stackable block;
(c) at least one electrical connection contact comprising:
(i) a C-shaped contact portion disposed within the at least one pin receiving portion, the C-shaped contact portion having elastic properties; and
(ii) a lead portion disposed at a location exterior to the stackable block,
wherein the C-shaped contact portion and the lead portion integrally form the at least one electrical connection contact; and
(d) a seal component associated with each of the at least one pin receiving portion, the seal component comprising a vertical seal portion and a horizontal seal portion; and
wherein the at least one stackable block comprises at least one retaining clip for retaining the seal component.

22. The apparatus of claim 21, wherein the electrical connection contact comprises a precious metal.

23. The apparatus of claim 21, wherein the C-shaped contact portion comprises an unconstrained diameter that is smaller than an outer diameter of a pin insertable into the at least one pin receiving portion.

24. The apparatus of claim 21, further comprising at least one end block configured to couple with the at least one stackable block.

25. The apparatus of claim 24, further comprising an external clip configured to secure the end block and the least one stackable block.

26. The apparatus of claim 21, wherein the vertical seal portion comprises a first end and a second end, wherein the first end is configured to contact one of the at least one stackable blocks and the second is configured to contact another of the at least one stackable blocks.

27. The apparatus of claim 21, wherein the horizontal seal portion comprises a first end and a second end, wherein the first end is configured to contact a pin disposed in the pin receiving portion and the second end is configured to contact one of the at least one stackable blocks.

28. The apparatus of claim 27, whereby the horizontal seal creates a seal between two of the at least one stackable blocks.

29. An electrical connection apparatus comprising:
(a) at least one stackable block , wherein each block is operably coupleable to another stackable block;
(b) at least one means for receiving an insertable pin, the means for receiving the insertable pin defined by the at least one stackable block; and
(c) at least one means for providing an electrical connection between an insertable pin and an external device, the means for providing the electrical connection disposed in the at least one stackable block, wherein the at least one means for providing an electrical connection comprises:

(i) means for contacting the insertable pin disposed within the means for receiving the insertable pin, the means for contacting the insertable pin having elastic properties; and
(ii) exterior means for contacting the external device, the exterior means being electrically coupled to the means for contacting the insertable pin and;
(d) means for adjusting the means for contacting the insertable pin between an insertion position and a contact position.

30. A method of electrically connecting an implanted medical device and an implanted stimulation electrode, the method comprising:
providing a connection device comprising at least one stackable block and a first end block and a second end block arranged on a first and a second end of the at least one stackable block, each of the at least one stackable blocks comprising:
(a) at least one pin receiving portion defined by the stackable block; and
(b) at least one electrical connection contact comprising:
(i) a C-shaped contact portion disposed within the at least one pin receiving portion, the C-shaped contact portion having elastic properties; and
(ii) a lead portion disposed at a location exterior to the stackable block;
inserting a pin into the at least one pin receiving portion, wherein the pin is electrically coupled to one of the implanted medical device or the implanted stimulation electrode;
electrically coupling to the lead portion the other of the implanted medical device or the implanted stimulation electrode; and
rotating an adjustment component disposed within each of the at least two stackable blocks, whereby the C-shaped contact portion moves between a contact position in contact with the pin and an insertion position.

* * * * *